US012654067B2

(12) United States Patent
Ahn et al.

(10) Patent No.: US 12,654,067 B2
(45) Date of Patent: Jun. 16, 2026

(54) ELECTRONIC DEVICE AND WEARABLE DEVICE FOR PROVIDING EXERCISE PROGRAM, AND CONTROL METHOD OF THE SAME

(71) Applicant: Samsung Electronics Co., Ltd., Suwon-si (KR)

(72) Inventors: Chiyoung Ahn, Suwon-si (KR); Joayoung Lee, Suwon-si (KR); Harkjoon Kim, Suwon-si (KR); Seungjoon Lee, Suwon-si (KR); Hoon Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 213 days.

(21) Appl. No.: 18/498,840

(22) Filed: Oct. 31, 2023

(65) Prior Publication Data

US 2024/0123291 A1 Apr. 18, 2024

Related U.S. Application Data

(63) Continuation of application No. PCT/KR2023/012792, filed on Aug. 29, 2023.

(30) Foreign Application Priority Data

Oct. 4, 2022 (KR) ........................ 10-2022-0126521
Dec. 15, 2022 (KR) ........................ 10-2022-0176145

(51) Int. Cl.
*A63B 24/00* (2006.01)
*A61B 5/11* (2006.01)
*A63B 71/06* (2006.01)

(52) U.S. Cl.
CPC ........ *A63B 24/0075* (2013.01); *A61B 5/1116* (2013.01); *A63B 24/0062* (2013.01);
(Continued)

(58) Field of Classification Search
CPC ............ A63B 24/0075; A63B 24/0062; A63B 2024/0065
See application file for complete search history.

(56) References Cited

U.S. PATENT DOCUMENTS 9,259,615 B2 2/2016 Weast et al.
9,757,640 B2 9/2017 Weast et al.
(Continued)

FOREIGN PATENT DOCUMENTS

CN 102614066 A 8/2012
JP 7054130 B2 4/2022
(Continued)

OTHER PUBLICATIONS

Cairns et al., Central activation, metabolites, and calcium handling during fatigue with repeated maximal isometric contractions in human muscle, Eur J Appl Physiol, DOI 10.1007/s00421-017-3640-y, Published May 19, 2017, 15 pages, Springer.
(Continued)

*Primary Examiner* — Joshua T Kennedy
(74) *Attorney, Agent, or Firm* — Nixon & Vanderhye P.C.

(57) ABSTRACT

An electronic device and/or a wearable device providing an exercise program, and/or a control method thereof are provided. The electronic device may include a communication module configured to communicate with the wearable device. The electronic device may include at least one processor. The processor may provide a first exercise program of a first exercise period according to an initial exercise intensity range to a user wearing the wearable device. The processor may measure a first posture score of the user while the user is performing the first exercise program. The processor may compare the first posture score to a posture boundary value. The processor may set a personal exercise intensity range of the user based on a result of the comparing. The processor may provide a second exercise program
(Continued)

of a second exercise period according to the personal exercise intensity range.

20 Claims, 31 Drawing Sheets

(52) U.S. Cl.
CPC .. *A63B 71/0622* (2013.01); *A63B 2024/0065* (2013.01); *A63B 2220/836* (2013.01); *A63B 2225/20* (2013.01)

(56) References Cited

U.S. PATENT DOCUMENTS

| | | | |
|---|---|---|---|
| 10,456,623 B2 | 10/2019 | Weast et al. | |
| 2016/0022440 A1* | 1/2016 | Ha | A61H 3/00 |
| | | | 623/24 |
| 2017/0027801 A1* | 2/2017 | Choi | A61B 5/024 |
| 2017/0027802 A1* | 2/2017 | Jang | A61H 1/0244 |
| 2017/0063278 A1* | 3/2017 | Roh | H02H 7/0854 |
| 2018/0085281 A1* | 3/2018 | Roh | A61H 3/06 |
| 2018/0116827 A1* | 5/2018 | Lim | A63B 23/0405 |
| 2018/0235831 A1* | 8/2018 | Jang | A61B 5/7264 |
| 2018/0353810 A1 | 12/2018 | Kim et al. | |
| 2020/0015712 A1* | 1/2020 | Hayashida | G08B 21/0446 |
| 2021/0121354 A1* | 4/2021 | Seo | A63B 21/0058 |
| 2021/0121729 A1* | 4/2021 | Kim | A61H 1/0244 |
| 2021/0128972 A1* | 5/2021 | Lee | A63B 21/00178 |
| 2021/0162263 A1* | 6/2021 | Roh | H02P 27/06 |
| 2021/0200302 A1* | 7/2021 | Hyung | G06F 3/011 |
| 2021/0275856 A1* | 9/2021 | Mahoney | A63B 21/0552 |
| 2021/0353992 A1* | 11/2021 | Roh | A61H 3/00 |
| 2022/0143484 A1* | 5/2022 | Wang | G06N 20/00 |
| 2022/0284824 A1* | 9/2022 | Gerson | A61B 5/7455 |

FOREIGN PATENT DOCUMENTS

| | | |
|---|---|---|
| KR | 101694402 B1 | 1/2017 |
| KR | 10-2021-0050268 A | 5/2021 |
| KR | 10-2021-0053976 A | 5/2021 |
| KR | 20210153505 A | 12/2021 |
| KR | 10-2022-0090261 A | 6/2022 |
| KR | 102411138 B1 | 6/2022 |
| WO | WO 2022/191435 A | 9/2022 |

OTHER PUBLICATIONS

Tsurubami et al., Warm-Up Intensity and Time Course Effects on Jump Performance, Journal of Sports Science and Medicine, Published Nov. 19, 2020, pp. 714-720.

PCT International Search Report dated Dec. 4, 2023 for PCT/KR2023/012792.

Extended European Search Report dated Jul. 7, 2025 issued in European Patent Application No. 23875055.8, 11 pp.

\* cited by examiner

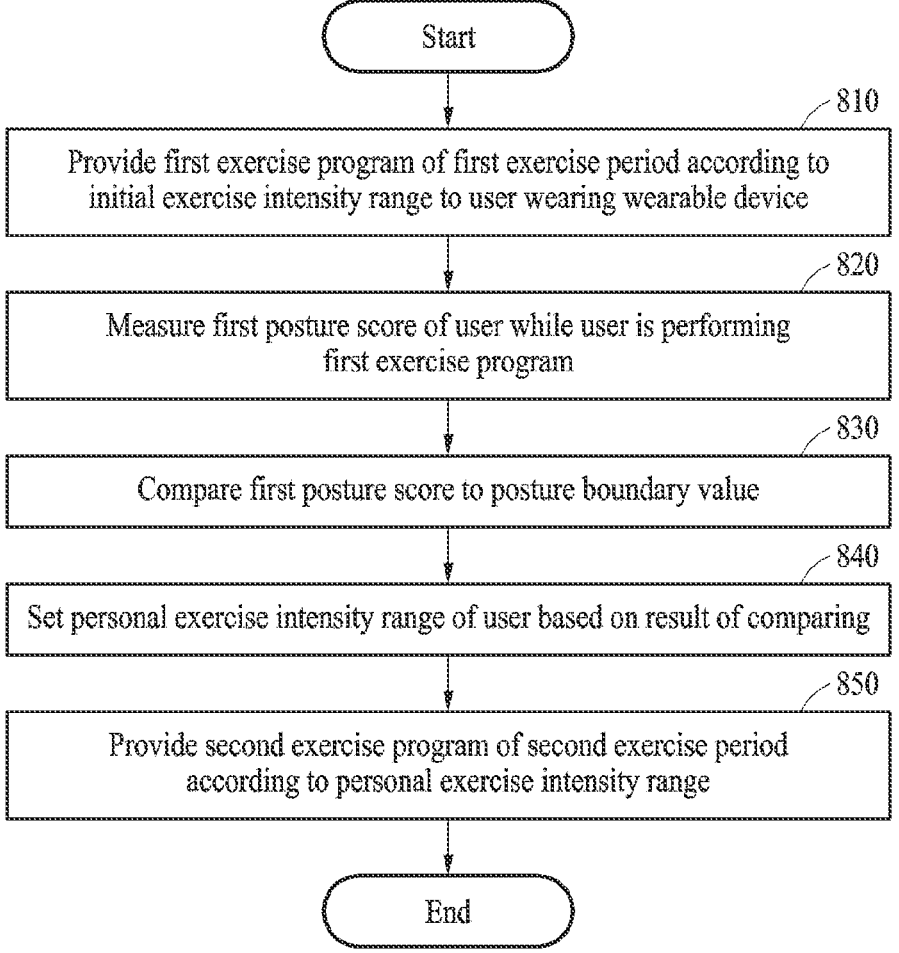

Start

810
Provide first exercise program of first exercise period according to
initial exercise intensity range to user wearing wearable device 820
Measure first posture score of user while user is performing
first exercise program 830
Compare first posture score to posture boundary value 840
Set personal exercise intensity range of user based on result of comparing 850
Provide second exercise program of second exercise period
according to personal exercise intensity range End

FIG. 8

Actuator torque          Motion tempo          Motion range 1621  1622

1801

2110

2120

2130

2140

ELECTRONIC DEVICE AND WEARABLE DEVICE FOR PROVIDING EXERCISE PROGRAM, AND CONTROL METHOD OF THE SAME

CROSS-REFERENCE TO RELATED APPLICATIONS

This application is a continuation of International Application No. PCT/KR2023/012792 designating the United States, filed on Aug. 29, 2023, in the Korean Intellectual Property Receiving Office and claiming priority to Korean Patent Application No. 10-2022-0126521 filed on Oct. 4, 2022, and Korean Patent Application No. 10-2022-0176145 filed on Dec. 15, 2022, in the Korean Intellectual Property Office, the disclosures of which are all hereby incorporated by reference herein in their entireties.

BACKGROUND

1. Field

Certain embodiments relate to an electronic device and/or a wearable device for providing an exercise program, and/or a method of controlling the same.

2. Description of Related Art

Weight training refers to an exercise that provides repeated stimulations to muscles to build muscle. Users may efficiently perform weight training with the assistance of a trainer. Users may efficiently perform weight training through fitness applications or videos.

SUMMARY

According to an example embodiment, an electronic device may include a communication module, comprising communication circuitry, configured to communicate with a wearable device. The electronic device may include a processor comprising processing circuitry. The processor may provide a first exercise program of a first exercise period according to an initial exercise intensity range to a user wearing the wearable device. The processor may measure a first posture score of the user while the user is performing the first exercise program. The processor may compare the first posture score to a posture boundary value. The processor may set a personal exercise intensity range of the user based on a result of the comparing. The processor may provide a second exercise program of a second exercise period according to the personal exercise intensity range.

According to an example embodiment, a control method may include providing a first exercise program of a first exercise period according to an initial exercise intensity range to a user wearing a wearable device. The control method may include measuring a first posture score of the user while the user is performing the first exercise program. The control method may include comparing the first posture score to a posture boundary value. The control method may include setting a personal exercise intensity range of the user based on a result of the comparing. The control method may include providing a second exercise program of a second exercise period according to the personal exercise intensity range. The providing of the second exercise program may include measuring a second posture score of the user while the user is performing the second exercise program. The providing of the second exercise program may include adjusting a current exercise intensity of the second exercise program in response to the second posture score being out of a control margin of the posture boundary value.

According to an example embodiment, a wearable device may include a leg support frame configured to support a leg of a user when the wearable device is worn on the leg of the user. The wearable device may include a driving module, comprising a motor and/or circuitry, configured to generate an exercise load for a motion of the user. The wearable device may include a processor. The processor may provide a first exercise program of a first exercise period according to an initial exercise intensity range to the user. The processor may measure a first posture score of the user while the user is performing the first exercise program. The processor may compare the first posture score to a posture boundary value. The processor may set a personal exercise intensity range of the user based on a result of the comparing. The processor may provide a second exercise program of a second exercise period according to the personal exercise intensity range.

BRIEF DESCRIPTION OF THE DRAWINGS

These and/or other aspects, features, and advantages will become apparent and more readily appreciated from the following description of example embodiments, taken in conjunction with the accompanying drawings of which:

FIG. 8 is a flowchart illustrating a control method according to an example embodiment.

DETAILED DESCRIPTION

Figure 1:
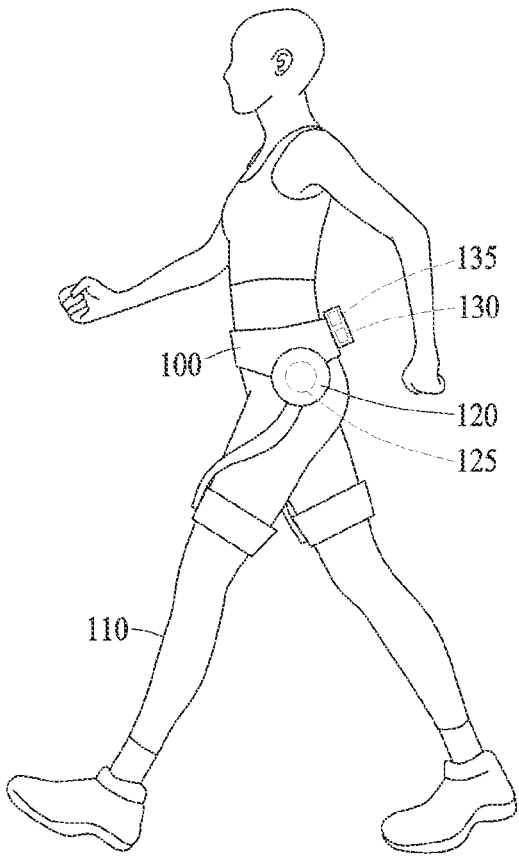
FIG. 1 is a diagram illustrating an overview of a wearable device worn on a body of a user according to an example embodiment.

The following detailed structural or functional descriptions are provided only as examples, and various changes, alterations, and modifications may be made to example embodiments. Accordingly, the example embodiments are not construed as limited to the disclosure and should be understood to include all changes, equivalents, and replacements within the idea and the technical scope of the disclosure.

As used herein, the singular forms "a," "an," and "the" include the plural forms as well, unless the context clearly indicates otherwise. It will be further understood that the terms "comprises/comprising" and/or "includes/including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms, including technical and scientific terms, used herein have the same meaning as commonly understood by one of ordinary skill in the art to which the present disclosure pertains. Terms, such as those defined in commonly used dictionaries, are to be interpreted as having meanings that are consistent with their meanings in the context of the relevant art and are not to be interpreted in an idealized or overly formal sense unless expressly so defined herein.

Hereinafter, the example embodiments will be described in detail with reference to the accompanying drawings. When describing the example embodiments with reference to the accompanying drawings, like reference numerals refer to like elements and a repeated description related thereto will be omitted.

FIG. 1 is a diagram illustrating an overview of a wearable device worn on a body of a user according to an example embodiment.

Referring to FIG. 1, according to an example embodiment, a wearable device 100 may be a device worn on a body of a user 110 to assist the user 110 in walking, exercising, and/or working. In an example embodiment, the wearable device 100 may also be used to measure a physical ability (e.g., a walking ability and an exercise ability) of the user 110. In some example embodiments, the term "wearable device" may be replaced with a "wearable robot," a "walking assistance device," or an "exercise assistance device." The user 110 may be a human or an animal but is not limited thereto. The wearable device 100 may be worn on the body of the user 110 (e.g., a lower body (legs, ankles, knees, etc.), an upper body (torso, arms, wrists, etc.), or a waist) to apply an external force such as an assistance force and/or a resistance force to a body movement or motion of the user 110. The assistance force, which is a force applied in the same direction as a body motion of the user 110, may be a force that assists the user 110 with the body motion. The resistance force, which is a force applied in an opposite direction of a body motion of the user 110, may be a force that hinders the body motion of the user 110. The resistance force may also be referred to as an exercise load.

In an example embodiment, when the wearable device 100 operates in a walking assistance mode for assisting the user 110 in walking, the wearable device 100 may assist the user 110 in walking by applying an assistance force generated from a driving module 120 (comprising a motor and/or circuitry) of the wearable device 100 to the body of the user 110. The wearable device 100 may provide a force required for the user 110 to walk to allow the user 110 to walk independently or for a long time, thereby expanding the walking ability of the user 110. The wearable device 100 may contribute to improving a gait of a pedestrian who has an abnormal walking habit or walking posture.

In an example embodiment, when the wearable device 100 operates in an exercise assistance mode for enhancing an exercise effect for the user 110, the wearable device 100 may hinder a body motion of the user 110 or provide resistance to the body motion of the user 110 by applying a resistance force generated from the driving module 120 to the body of the user 110. In a case in which the wearable device 100 is a hip-type wearable device worn on the waist (or pelvis) and legs (e.g., thighs) of the user 110, the wearable device 100 may provide an exercise load to a body motion of the user and enhance an exercise effect on the legs of the user 110, while worn on the legs. In an example embodiment, the wearable device 100 may apply the assistance force to the body of the user 110 to assist the user 110 with a body motion of the user 110 in the exercise assistance mode. In an example embodiment, the wearable device 100 may combine and provide the assistance force and the resistance force for each exercise period or for each time period, for example, by providing the assistance force in some exercise periods and providing the resistance force in some exercise periods in the exercise assistance mode.

In an example embodiment, when the wearable device 100 operates in a physical ability measurement mode for measuring a physical ability of the user 110, the wearable device 100 may measure motion information of the user 110 using sensors (e.g., an angle sensor 125 and an inertial measurement unit (IMU) 135) provided in the wearable device 100 while the user 110 is walking or exercising, and evaluate a physical ability of the user 110 based on the measured motion information.

In various example embodiments, for the convenience of description, a hip-type wearable device shown in FIG. 1 is described as an example of the wearable device 100, but examples of which are not limited thereto. As described above, the wearable device 100 may be worn on other body parts (e.g., upper arms, lower arms, hands, calves, and feet) other than the waist and the legs (e.g., the thighs in particular), and may vary in shape and configuration depending on a body part on which the wearable device 100 is worn.

Figure 3:
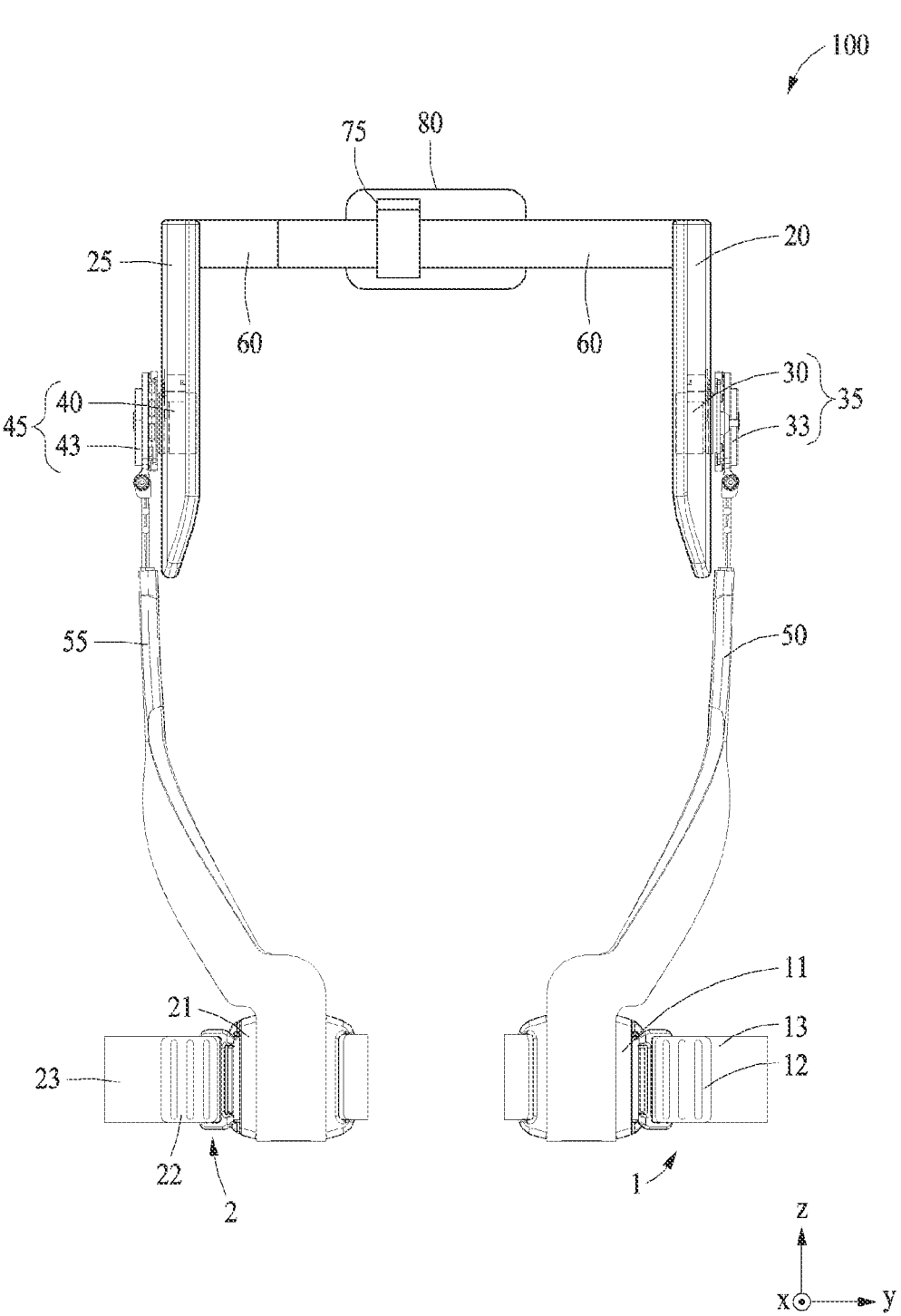
FIG. 3 is a front view of a wearable device according to an example embodiment.

According to an example embodiment, the wearable device 100 may include a support frame (e.g., leg support frames 50 and 55 and waist support frames 20 and 25 of FIG. 3) configured to support the body of the user 110 when the wearable device 100 is worn on the body of the user 110, a sensor module (e.g., a sensor module 520 of FIG. 5A, comprising at least one sensor) configured to obtain sensor data including motion information associated with a body motion (e.g., a leg motion and an upper body motion) of the user 110, the driving module 120 (e.g., driving modules 35 and 45 of FIG. 3, each driving module comprising at least one of a motor and/or circuitry) configured to generate an external force to be applied to the legs of the user 110, and a control module 130 comprising processing circuitry (e.g., a control module 510 of FIGS. 5A and 5B) configured to control the wearable device 100.

The sensor module may include the angle sensor 125 and the IMU 135. The angle sensor 125 may measure a hip joint angle value of the user 110. The angle sensor 125 may include, for example, an encoder and/or a hall sensor. In an example embodiment, the angle sensor 125 may be disposed near a left hip joint and a right hip joint each and measure a hip joint angle value of the left hip joint and a hip joint angle value of the right hip joint of the user 110. The hip joint angle value of the left hip joint may correspond to an angle of a left leg of the user 110, and the hip joint angle value of the right hip joint may correspond to an angle of a right leg of the user 110. The IMU 135 may measure a change in acceleration and rotation speed by a movement or motion of the user 110. For example, the IMU 135 may measure an upper body motion value of the user 110. The IMU 135 may include an acceleration sensor and/or an angular velocity sensor.

In an example embodiment, the control module 130 and the IMU 135 may be disposed in a housing (e.g., a housing 80 of FIG. 3) of the wearable device 100. The housing may be formed or attached to the outside of the support frame of the wearable device 100 and may be disposed behind the waist when the user 110 wears the wearable device 100, but examples are not limited thereto.

Figure 2:
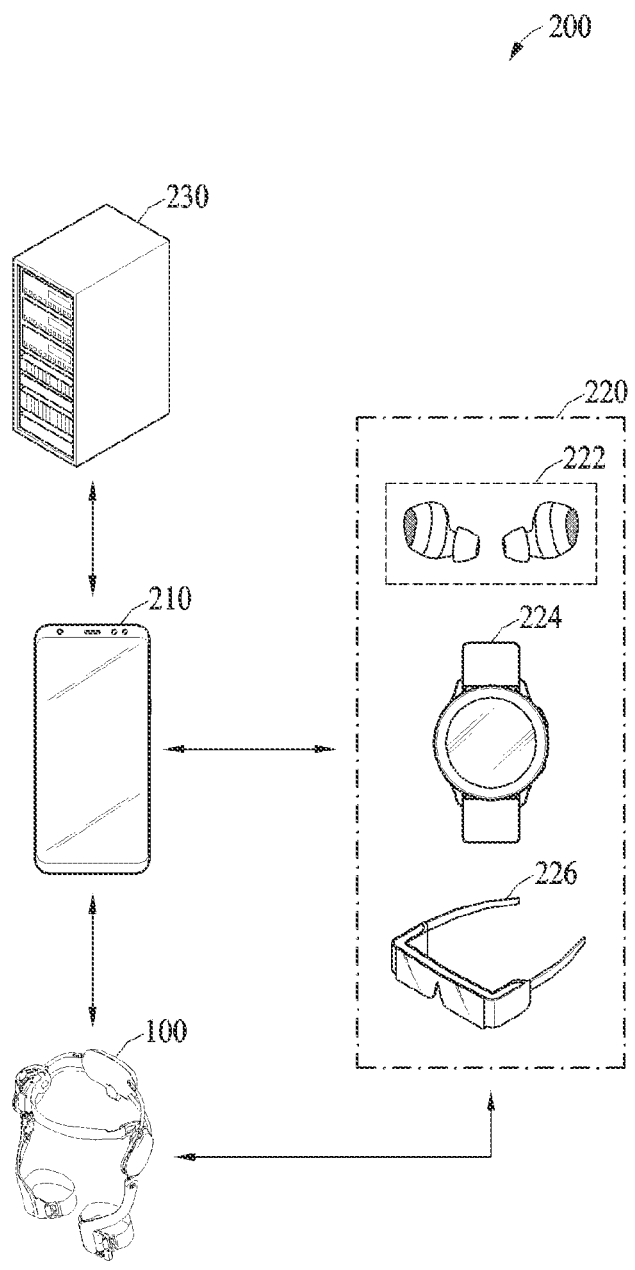
FIG. 2 is a diagram illustrating a management system including a wearable device and an electronic device according to an example embodiment.

In an example embodiment, the wearable device 100 may provide a physical ability measurement (or evaluation) function of measuring (or evaluating) a physical ability of the user 110 by interworking with an electronic device (e.g., an electronic device 210 of FIG. 2). When the user 110 performs motions according to a guide provided through a program (e.g., an application) executed on the electronic device while the wearable device 100 is worn on the user 110, the wearable device 100 may obtain sensor data from the motions through the sensor module. The electronic device may analyze the sensor data obtained by the wearable device 100 to estimate the physical ability (e.g., walking ability, muscular strength, fall possibility, etc.), and provide physical ability information about the estimated physical ability to the user 110. The electronic device and the wearable device 100 may provide various measurement methods (e.g., a walking ability test, a timed up and go (TUG) test, a five times sit to stand (5×STS) test, and a short physical performance battery (SPPB) test) to measure a user's physical ability. As one of the measurement methods, a new measurement method may be added, or a detailed process of an existing measurement method may be updated to be used. The user 110 may select a measurement method to be performed, and a guide for performing the measurement method selected by the user 110 may be provided to the user 110.

The wearable device 100 and the electronic device may periodically measure a user's physical ability and provide physical ability information to a user. In an example embodiment, the physical ability information of the user may be transferred to a terminal of a person registered in the electronic device (e.g., a family member, medical staff, and an exercise instructor).

FIG. 2 is a diagram illustrating a management system including a wearable device and an electronic device according to an example embodiment.

Referring to FIG. 2, a management system 200 may include a wearable device 100 for assisting a user with a body motion, an electronic device 210, another wearable device 220, and a server 230. In an example embodiment, at least one of these devices (e.g., the other wearable device 220 or the server 230) may be omitted from, or one or more other devices (e.g., a dedicated controller device for the wearable device 100) may be added to the management system 200.

In an example embodiment, in a walking assistance mode, the wearable device 100 may assist the user with a motion while worn on a body of the user. For example, the wearable device 100 may assist the user in walking by generating an assistance force for assisting the user with a leg motion while worn on the legs of the user. In an example embodiment, in an exercise assistance mode, the wearable device 100 may generate a resistance force for hindering a body motion of the user and apply the resistance force to the body of the user to enhance an exercise effect on the user.

In an example embodiment, the wearable device 100 may be used to measure a physical ability of the user by interworking with the electronic device 210. The wearable device 100 may operate in a physical ability measurement mode, which is a mode for measuring the physical ability of the user, under the control of the electronic device 210, and may transmit sensor data obtained from a motion of the user in the physical ability measurement mode to the electronic device 210. The electronic device 210 may analyze the sensor data received from the wearable device 100 and estimate the physical ability of the user.

The electronic device 210 may communicate with the wearable device 100, remotely control the wearable device 100, or provide state information (e.g., a remaining battery level) of the wearable device 100 to the user. The electronic device 210 may receive sensor data obtained by a sensor of the wearable device 100 from the wearable device 100 and may determine a physical condition or physical ability of the user based on the received sensor data. In an example embodiment, the electronic device 210 may execute a program (e.g., an application) for controlling the wearable device 100, and the user may adjust operations or set values (e.g., a magnitude of torque and an audio volume) of the wearable device 100 through the program. According to an example embodiment, the electronic device 210 may be provided in various types. The electronic device 210 may include, as non-limiting examples, a portable communication device (e.g., a smartphone), a computer device, a portable multimedia device, or a home appliance device.

According to an example embodiment, the electronic device 210 may be connected to the server 230 using short-range wireless communication or cellular communication. The server 230 may receive user information (e.g., name, age, gender) and/or physical ability information of the user using the wearable device 100 from the electronic device 210, and store and manage the received user information and/or physical ability information. The server 230 may provide the electronic device 210 with various exercise programs or physical ability measurement programs that are to be provided to the user by the wearable device 100.

According to an example embodiment, the wearable device 100 and/or the electronic device 210 may be connected, directly or indirectly, to the other wearable device 220. The other wearable device 220 may include, as non-limiting examples, wireless earphones 222, a smartwatch 224, or smart glasses 226. In an example embodiment, the physical ability information generated by the electronic device 210 and/or the state information of the wearable device 100 may be transmitted to the other wearable device 220 to be provided to the user through the other wearable device 220. In an example embodiment, the wearable device 100, the electronic device 210, and the other wearable device 220 may be connected to each other through wireless communication (e.g., Bluetooth communication).

Figure 4:
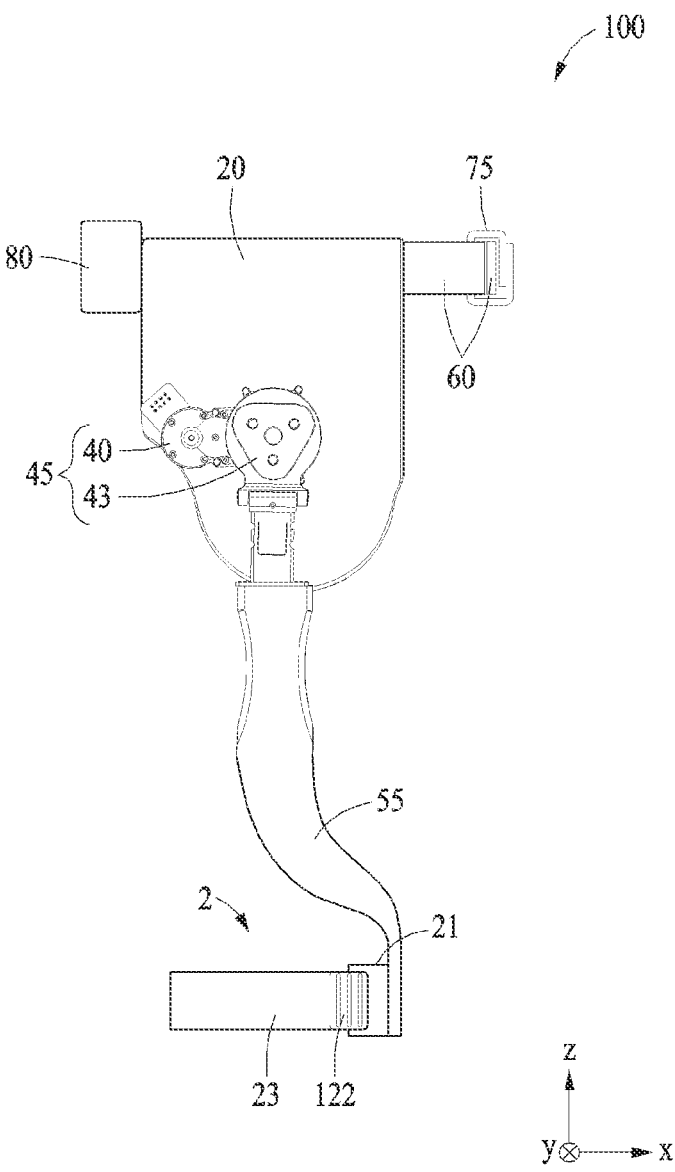
FIG. 4 is a side view of a wearable device according to an example embodiment.

FIG. 3 is a front view of a wearable device according to an example embodiment, and FIG. 4 is a side view of a wearable device according to an example embodiment.

Referring to FIGS. 3 and 4, according to an example embodiment, a wearable device 100 worn on a body of a user may include a housing 80, waist support frames 20 and 25, driving modules 35 and 45, leg support frames 50 and 55, thigh fastening portions 1 and 2, and a waist fastening portion. The waist fastening portion may include a belt 60 and an auxiliary belt 75. In an example embodiment, at least one of these components (e.g., the auxiliary belt 75) may be omitted from, or one or more other components (e.g., a fastening detection module for detecting whether the thigh fastening portions 1 and 2 or the waist fastening portion are fastened) may be added to the wearable device 100.

In an example embodiment, in the housing 80, a control module (not shown) (e.g., the control module 130 of FIG. 1 or a control module 510 of FIGS. 5A and 5B, each of which may comprise at least one processor), an IMU (not shown) (e.g., the IMU 135 of FIG. 1), and a battery (not shown) may be disposed. The housing 80 may protect the control module, the IMU, and the battery. For example, the housing 80 may be disposed on the back of the user or a back side of a waist of the user, based on a state in which the wearable device 100 is worn on a body of the user. The control module may generate a control signal for controlling the wearable device 100 and control an operation of the wearable device 100 based on the control signal. The control module may include a control circuit including a processor, a memory, and a communication module to control actuators 30 and 40 of the driving modules 35 and 45. The control module may further include a power supply module (not shown) configured to supply power of the battery to each component of the wearable device 100.

In an example embodiment, the wearable device 100 may include a sensor module (not shown) (e.g., a sensor module 520 of FIG. 5A) configured to obtain sensor data from one or more sensors. The sensor module may obtain sensor data that varies according to a motion of the user. In an example embodiment, the sensor module may obtain sensor data including motion information of the user in a physical ability measurement mode for measuring a physical ability of the user. The sensor module may include, as non-limiting examples, an IMU (e.g., the IMU 135 of FIG. 1) for measuring an upper body motion value of the user and an angle sensor (e.g., the angle sensor 125 of FIG. 1) for measuring a hip joint angle value of the user. For example, the sensor module may further include at least one of a position sensor, a temperature sensor, a biosignal sensor, or a proximity sensor.

In an example embodiment, the waist support frames 20 and 25 may support a part of the body of the user when the wearable device 100 is worn on the body of the user. The waist support frames 20 and 25 may contact at least a portion of an outer surface of the user. The waist support frames 20 and 25 may be provided in a curved shape corresponding to the contact portion of the body of the user. The waist support frames 20 and 25 may be provided in, for example, a shape that surrounds the outer surface of the waist (or pelvis) of the user to support the waist or pelvis of the user. The waist support frames 20 and 25 may include a first waist support frame 25 for supporting a right side of the waist of the user, and a second waist support frame 20 for supporting a left side of the waist of the user. The waist support frames 20 and 25 may be connected, directly or indirectly, to the housing 80.

The waist fastening portion may be connected, directly or indirectly, to the waist support frames 20 and 25 to fix the waist support frames 20 and 25 to the waist of the user. The waist fastening portion may include, for example, a pair of belts 60 and an auxiliary belt 75. The auxiliary belt 75 may be connected, directly or indirectly, to one of the belts 60.

In an example embodiment, the pair of belts 60 may be connected, directly or indirectly, to the waist support frames 20 and 25. The pair of belts 60 may maintain a shape extending forward (e.g., +x direction) in a state before the user wears the wearable device 100 not to hinder the user from entering the waist support frame 20. Once the user enters the pair of waist support frames 20 and 25, the pair of belts 60 may be deformed to surround a front portion of the user. The waist support frames 20 and 25 and the pair of belts 60 may wrap around the waist of the user overall. In an example embodiment, the auxiliary belt 75 may fix the belts 60 to each other while the belts 60 overlap each other. For example, one of the belts 60 may wrap the other together with the auxiliary belt 75.

The driving modules 35 and 45 may generate an external force (or torque) to be applied to the body of the user based on a control signal generated by the control module. For example, the driving modules 35 and 45 may generate an external force to be applied to the legs of the user under the control of the control module. In an example embodiment, the driving modules 35 and 45 may include a first driving module 45 disposed at a position corresponding to a right hip joint of the user and a second driving module 35 disposed at a position corresponding to a left hip joint of the user. The first driving module 45 may include a first actuator 40 and a first joint member 43, and the second driving module 35 may include a second actuator 30 and a second joint member 33. The first actuator 40 may provide power to be transmitted to the first joint member 43, and the second actuator 30 may provide power to be transmitted to the second joint member 33. The first actuator 40 and the second actuator 30 may each include a motor configured to generate power (or torque) by receiving power from the battery. When powered and driven, the motor may provide a force (e.g., an assistance force) for assisting the user with a body motion or a force (e.g., a resistance force) for hindering a body motion of the user. In an example embodiment, the control module may adjust an intensity and direction of the force generated by the motor by adjusting a voltage and/or current supplied to the motor.

In an example embodiment, the first joint member 43 and the second joint member 33 may receive power from the first actuator 40 and the second actuator 30, respectively, and apply an external force to the body of the user based on the received power. The first joint member 43 and the second joint member 33 may be disposed at positions corresponding to joint portions of the user, respectively. The first joint member 43 and the second joint member 33 may be disposed on one side of the waist support frames 25 and 20, respectively. One side of the first joint member 43 may be connected, directly or indirectly, to the first actuator 40, and another side of the first joint member 43 may be connected, directly or indirectly, to the first leg support frame 55. The first joint member 43 may be rotated by the power received from the first actuator 40. An encoder or a hall sensor that may operate as an angle sensor for measuring a rotation angle (corresponding to a joint angle of the user) of the first joint member 43 may be disposed on one side of the first joint member 43. One side of the second joint member 33 may be connected, directly or indirectly, to the second actuator 30, and another side of the second joint member 33 may be connected, directly or indirectly, to the second leg support frame 50. The second joint member 33 may be rotated by the power received from the second actuator 30. An encoder or a hall sensor that may operate as an angle sensor for measuring a rotation angle of the second joint member 33 may be disposed on one side of the second joint member 33.

In an example embodiment, the first actuator 40 may be disposed in a lateral direction of the first joint member 43, and the second actuator 30 may be disposed in a lateral direction of the second joint member 33. The first actuator 40 and the first joint member 43 may be disposed such that respective rotation axes thereof are spaced apart from each other, and the second actuator 30 and the second joint member 33 may also be disposed such that respective rotation axes thereof are spaced apart from each other. However, examples are not limited thereto, and the actuators 30 and 40 and the joint members 33 and 43 may share a rotation axis. In an example embodiment, the actuators 30 and 40 may be disposed to be spaced apart from the joint members 33 and 43, respectively. In this case, the driving modules 35 and 45 may each further include a power transmission module (not shown) configured to transmit power from the actuators 30 and 40 to the joint members 33 and 43. The power transmission module may be or comprise a rotary body such as a gear, or a longitudinal member such as a wire, a cable, a string, a spring, a belt, or a chain. However, the scope of example embodiments is not limited by a positional relationship between the actuators 30 and 40 and the joint members 33 and 43 and a power transmission structure that are described above.

In an example embodiment, the leg support frames 50 and 55 may support the legs (e.g., the thighs) of the user when the wearable device 100 is worn on the legs of the user. For example, the leg support frames 50 and 55 may transmit power generated by the driving modules 35 and 45 to the thighs of the user, and the power may act as an external force to be applied to a motion of the legs of the user. One end of the leg support frames 50 and 55 may be connected, directly or indirectly, to the joint members 33 and 43 to be rotated, and as another end of the leg support frames 50 and 55 is connected, directly or indirectly, to covers 11 and 21 of the thigh fastening portions 1 and 2, the leg support frames 50 and 55 may transmit the power generated by the driving modules 35 and 45 to the thighs of the user while supporting the thighs of the user. For example, the leg support frames 50 and 55 may push or pull the thighs of the user. The leg support frames 50 and 55 may extend in a longitudinal direction of the thighs of the user. The leg support frames 50 and 55 may be bent to wrap around at least a portion of a circumference of the thighs of the user. For example, upper portions of the leg support frames 50 and 55 may cover a portion of the body of the user that faces sideways (+y direction or −y direction), and lower portions of the leg support frames 50 and 55 may cover a portion of the body of the user that faces forward (+x direction). The leg support frames 50 and 55 may include a first leg support frame 55 for supporting a right leg of the user and the second leg support frame 50 for supporting a left leg of the user.

The thigh fastening portions 1 and 2 may be connected, directly or indirectly, to the leg support frames 50 and 55 and fix the leg support frames 50 and 55 to the thighs. The thigh fastening portions 1 and 2 may include a first thigh fastening portion 2 for fixing the first leg support frame 55 to a right thigh of the user and a second thigh fastening portion 1 for fixing the second leg support frame 50 to a left thigh of the user. The first thigh fastening portion 2 may include a first cover 21, a first fastening frame 22, and a first strap 23. The second thigh fastening portion 1 may include a second cover 11, a second fastening frame 12, and a second strap 13.

In an example embodiment, the covers 11 and 21 may apply torque generated by the driving modules 35 and 45 to the thighs of the user. For example, the covers 11 and 21 may be disposed on one side of the thighs of the user to push or pull the thighs of the user. The covers 11 and 21 may be disposed on, for example, a front surface of the thighs of the user. The covers 11 and 21 may be disposed in a circumferential direction of the thighs of the user. The covers 11 and 21 may extend to both sides from the other ends of the leg support frames 50 and 55 and may include curved surfaces corresponding to the thighs of the user. One end of the covers 11 and 21 may be connected, directly or indirectly, to the fastening frames 12 and 22, and the other end thereof may be connected, directly or indirectly, to the straps 13 and 23.

In an example embodiment, one end of the fastening frames 12 and 22 may be connected to one side of the covers 11 and 21, and the other end thereof may be connected to the straps 13 and 23. For example, the fastening frames 12 and 22 may be disposed to surround at least a portion of the circumference of the thighs of the user to prevent or reduce a chance of the thighs of the user from escaping from the leg support frames 50 and 55. The first fastening frame 22 may have a fastening structure that connects the first cover 21 and the first strap 23, and the second fastening frame 12 may have a fastening structure that connects the second cover 11 and the second strap 13.

The straps 13 and 23 may include an elastic material (e.g., a band) that may surround the rest of the thighs of the user that is not covered by the covers 11 and 21 and the fastening frames 12 and 22.

In an example embodiment, the wearable device 100 may support proximal and distal portions of the user to assist a relative movement between the proximal and distal portions. Among the components of the wearable device 100, components worn on the proximal portion of the user may be referred to as a "proximal wearable unit," and components worn on the distal portion of the user may be referred to as a "distal wearable unit." For example, among the components of the wearable device 100, the housing 80, the waist support frames 20 and 25, the pair of belts 60, and the auxiliary belt 75 may correspond to the proximal wearable unit, and the thigh fastening portions 1 and 2 may correspond to the distal wearable unit. For example, the proximal wearable unit may be worn on the waist or the pelvis of the user, and the distal wearable unit may be worn on the thighs or the calves of the user. However, positions at which the proximal wearable unit and the distal wearable unit are worn are not limited thereto. For example, the proximal wearable unit may be worn on the torso or the shoulder of the user, and the distal wearable unit may be worn on an upper arm or a lower arm of the user.

Figure 5A:
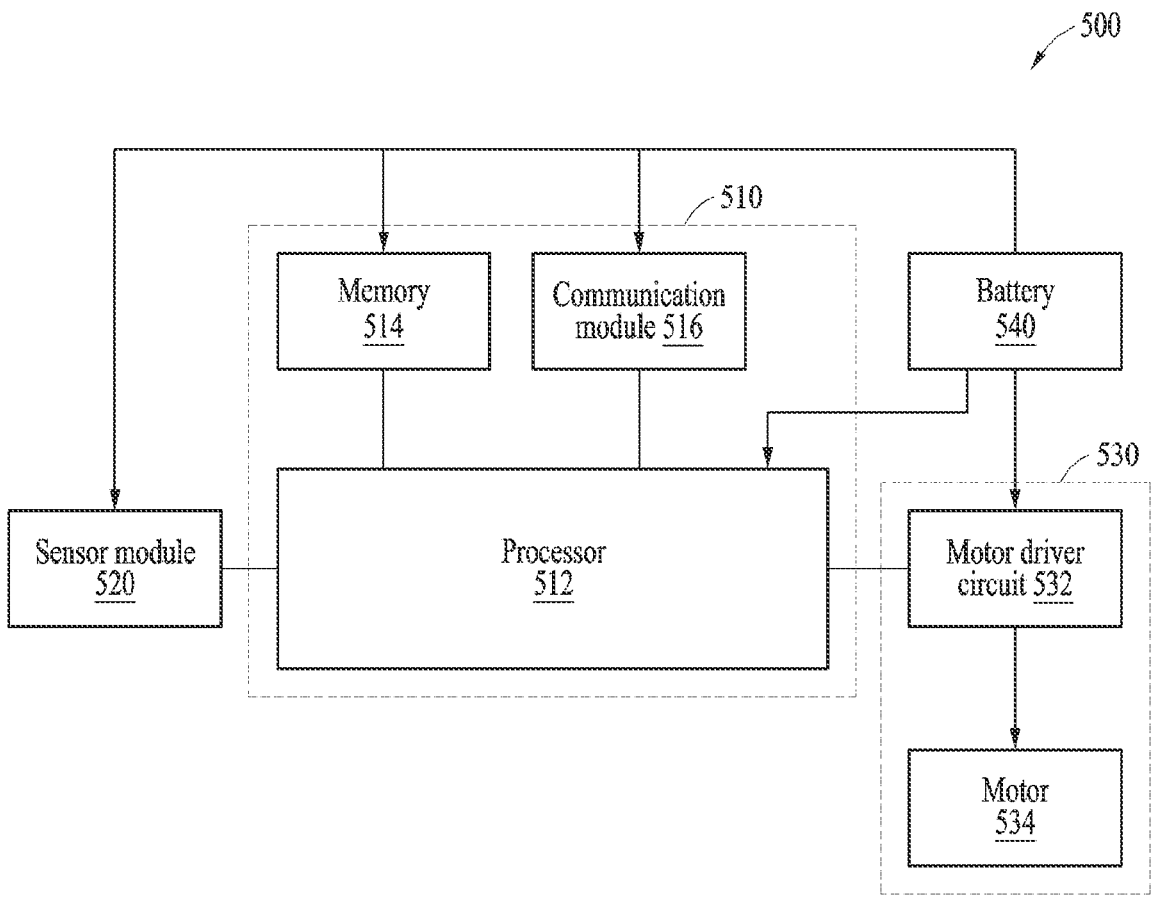
FIGS. 5A and 5B are diagrams illustrating a configuration of a control system of a wearable device according to an example embodiment.
Figure 5B:
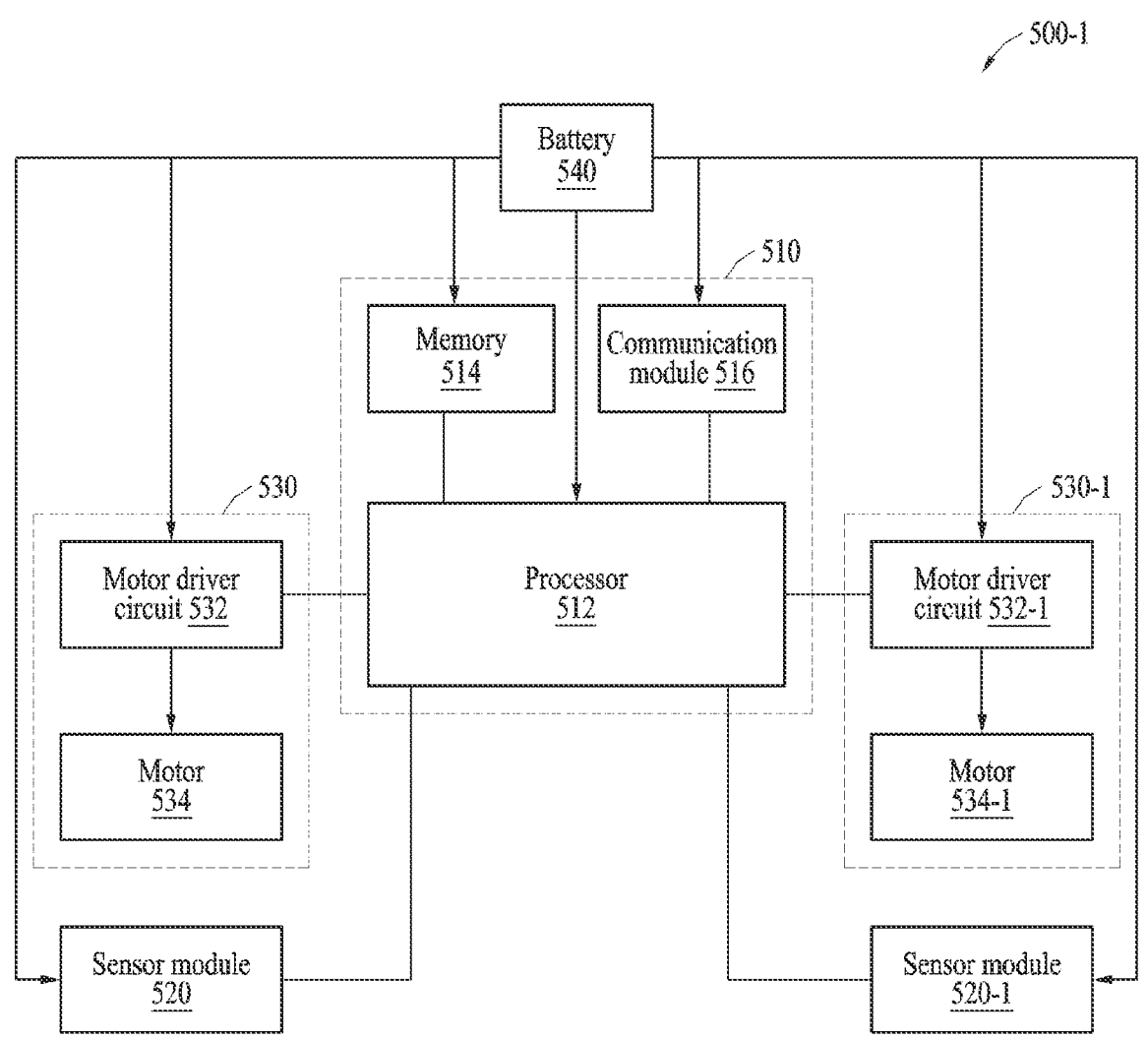

FIGS. 5A and 5B are diagrams illustrating a configuration of a control system of a wearable device according to an example embodiment.

Referring to FIG. 5A, a wearable device (e.g., the wearable device 100) may be controlled by a control system 500. The control system 500 may include a control module 510, a sensor module 520, a driving module 530, and a battery 540. The driving module 530 may include a motor 534 configured to generate power (e.g., torque) and a motor driver circuit 532 configured to drive the motor 534. Although one sensor module 520 and the driving module 530, including one motor driver circuit 532 and one motor 534, are shown in FIG. 5A, it is provided only as an example. Referring to FIG. 5B at 500-1, there may be a plurality of sensor modules 520 and 520-1, motor driver circuits 532 and 532-1, and motors 534 and 534-1. In this example, a driving module 530 including the motor driver circuit 532 and the motor 534 may correspond to the first driving module 45 of FIG. 3, and a driving module 530-1 including the motor driver circuit 532-1 and the motor 534-1 may correspond to the second driving module 35 of FIG. 3. The following description of each of the sensor module 520, the motor driver circuit 532, and the motor 534 may also be applied to the sensor module 520-1, the motor driver circuit 532-1, and the motor 534-1 shown in FIG. 5B.

Referring back to FIG. 5A, the sensor module 520 may include at least one sensor. The sensor module 520 may obtain sensor data that varies according to a motion of a user. For example, the sensor module 520 may include sensor data including motion information of the user in a physical ability measurement mode for measuring a physical ability of the user. The sensor module 520 may transmit the obtained sensor data to the control module 510. The sensor module 520 may include, for example, an IMU, an angle sensor (e.g., an encoder and a hall sensor), a position sensor, a proximity sensor, a biosignal sensor, and a temperature sensor. The IMU may measure an upper body motion value of the user. For example, the IMU may sense accelerations and angular velocities of an X-axis, a Y-axis, and a Z-axis according to a motion of the user. The angle sensor may measure a hip joint angle value according to a leg motion of the user. The sensor data measured by the angle sensor may include information about, for example, a hip joint angle value of a right leg, a hip joint angle value of a left leg, and a direction of a leg motion.

The battery 540 may supply power to each component of the wearable device. The wearable device may convert the power of the battery 540 according to an operating voltage of each component of the wearable device and supply the converted power to each component.

The driving module 530 may generate an external force to be applied to a leg of the user under the control of the control module 510. The driving module 530 may be disposed at a position corresponding to a hip joint of the user and may generate torque to be applied to the leg of the user based on a control signal generated by the control module 510. The control module 510 may transmit the control signal to the motor driver circuit 532, and the motor driver circuit 532 may generate a current signal corresponding to the control signal and supply the current signal to the motor 534 to control an operation of the motor 534. The current signal may not be supplied to the motor 534 according to the control signal. When being driven as the current signal is supplied to the motor 534, the motor 534 may generate a force for assisting the user with a leg motion or torque for hindering the leg motion of the user.

The control module 510 may control an overall operation of the wearable device and may generate a control signal to control each component (e.g., the driving module 530). The control module 510 may include at least one processor 512 comprising processing circuitry, a memory 514, and a communication module 516 comprising communication circuitry.

The processor 512 may execute, for example, software to control at least one other component (e.g., a hardware or software component) of the wearable device connected to the processor 512 and may perform various data processing or computation. According to an example embodiment, as at least a part of data processing or computation, the processor 512 may store instructions or data received from another component (e.g., the communication module 516) in the memory 514, process the instructions or data stored in the memory 514, and store result data obtained after the processing in the memory 514. According to an example embodiment, the processor 512 may include a main processor (e.g., a central processing unit (CPU) or an application processor (AP)) or an auxiliary processor (e.g., a graphics processing unit (GPU), a neural processing unit (NPU), an image signal processor (ISP), a sensor hub processor, or a communication processor (CP)) that is operable independently of, or in conjunction with, the main processor. The auxiliary processor may be implemented separately from the main processor or as a part of the main processor.

The memory 514 may store various data used by at least one component (e.g., the processor 512) of the control module 510. The data may include, for example, software, sensor data, and input data or output data for instructions related thereto. The memory 514 may include a volatile memory or a non-volatile memory (e.g., a random-access memory (RAM), a dynamic RAM (DRAM), or a static RAM (SRAM)).

The communication module 516 may support establishing a direct (e.g., wired) communication channel or a wireless communication channel between the control module 510 and another component of the wearable device or an external electronic device (e.g., the electronic device 210 or the other wearable device 220 of FIG. 2), and performing communication via the established communication channel. For example, the communication module 516 may transmit sensor data obtained by the sensor module 520 to an external electronic device (e.g., the electronic device 210 of FIG. 2) and receive a control signal from the electronic device. According to an example embodiment, the communication module 516 may include one or more CPs that are operable independently of the processor 512 and support direct (e.g., wired) communication or wireless communication. According to an example embodiment, the communication module 516 may include a wireless communication module (e.g., a cellular communication module, a short-range wireless communication module, or a global navigation satellite system (GNSS) communication module), and/or a wired communication module. A corresponding one of these communication modules may communicate with another component of the wearable device and/or an external electronic device via a short-range communication network such as Bluetooth™, wireless-fidelity (Wi-Fi), ANT, or infrared data association (IrDA), or a long-range communication network such as a legacy cellular network, a 5G network, a next-generation communication network, the Internet, or a computer network (e.g., a local area network (LAN) or a wide area network (WAN)).

In an example embodiment, the wearable device (e.g., the wearable device 100) may include a leg support frame (e.g., the leg support frames 50 and 55 and the waist support frames 20 and 25 of FIG. 3) for supporting the legs of the user when the wearable device is worn on the legs of the user. The wearable device may include a driving module (e.g., the driving module 120, the driving module 35, the driving module 45, the driving module 530, and/or the driving module 530-1) configured to generate an exercise load for a motion of the user (e.g., see FIGS. 1, 3, 5). The wearable device may include the processor 512. The processor 512 may provide the user with a first exercise program of a first exercise period according to an initial exercise intensity range. The processor 512 may measure a first posture score of the user while the user is performing the first exercise program. The processor 512 may compare the first posture score to a posture boundary value. The processor 512 may set a personal exercise intensity range of the user based on a comparison result obtained by the comparing. The processor 512 may provide a second exercise program of a second exercise period according to the personal exercise intensity range.

The posture boundary value may include an upper boundary value and a lower boundary value. The personal exercise intensity range may be determined by an upper intensity value and a lower intensity value.

To provide at least one of the first exercise program or the second exercise program, the processor 512 may display a virtual object on a display device and induce the user to perform a motion. The processor 512 may generate an exercise load for the motion of the user through the wearable device.

Figure 6A:
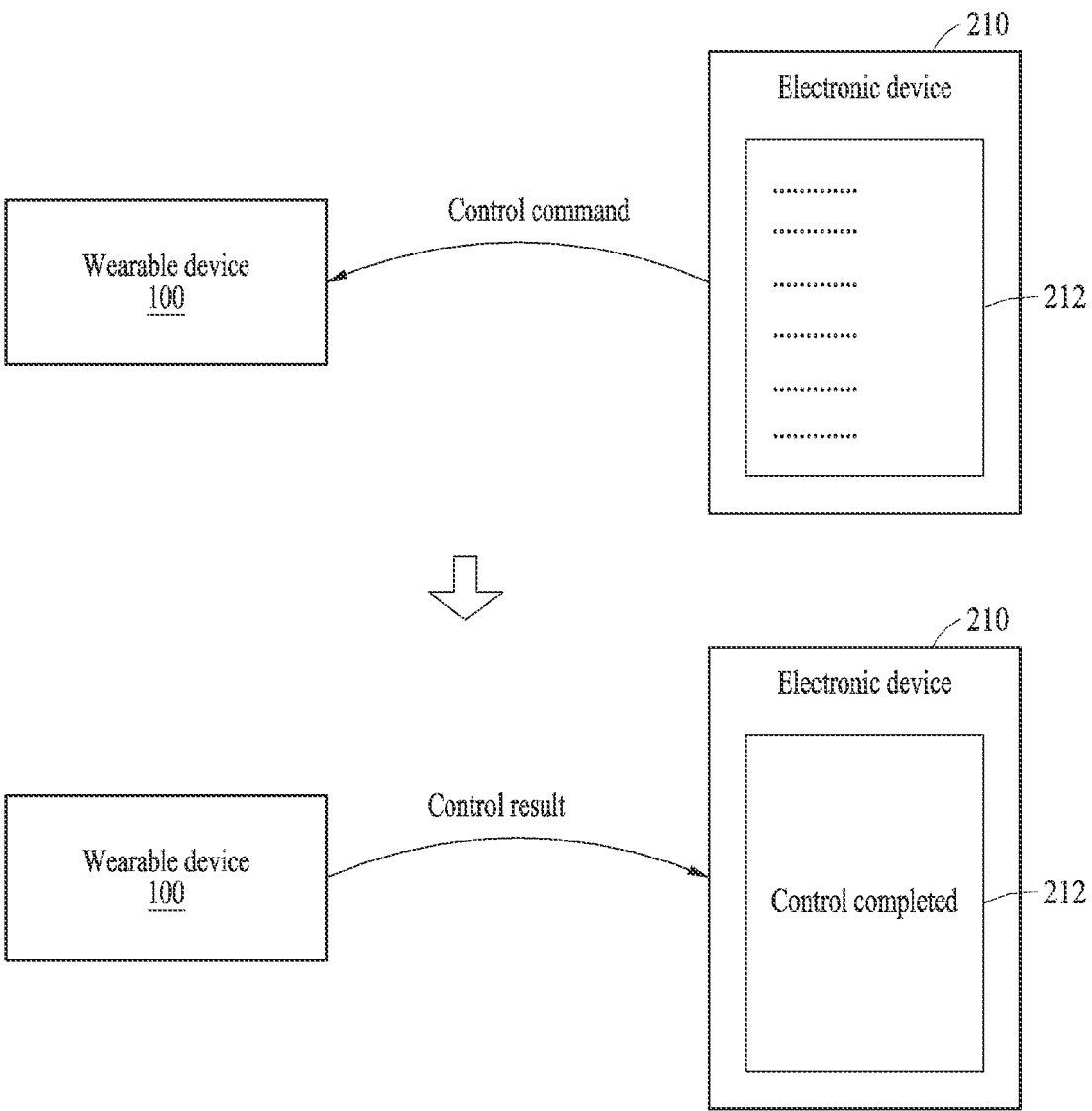
FIG. 6A is a diagram illustrating an interaction between a wearable device and an electronic device according to an example embodiment.

FIG. 6A is a diagram illustrating an interaction between a wearable device and an electronic device according to an example embodiment.

Referring to FIG. 6A, the wearable device 100 may communicate with the electronic device 210. For example, the electronic device 210 may be a user terminal of a user who uses the wearable device 100, or a dedicated controller for the wearable device 100. According to an example embodiment, the wearable device 100 and the electronic device 210 may be connected through short-range wireless communication.

The electronic device 210 may display, on a display 212, a user interface (UI) screen for controlling operations of the wearable device 100 or measuring a physical ability of the user. In an example embodiment, the user may input a command (e.g., a command for executing a physical ability measurement mode) for controlling the operations of the wearable device 100 through the UI screen on the display 212 of the electronic device 210. The electronic device 210 may generate a control command corresponding to the command and transmit the generated control command to the wearable device 100. The wearable device 100 may operate according to the received control command and transmit a control result and/or measured data (e.g., sensor data) to the electronic device 210. The electronic device 210 may provide result information (e.g., physical ability information) derived by analyzing the control result and/or data of the wearable device 100 to the user through the display 212.

Figure 6B:
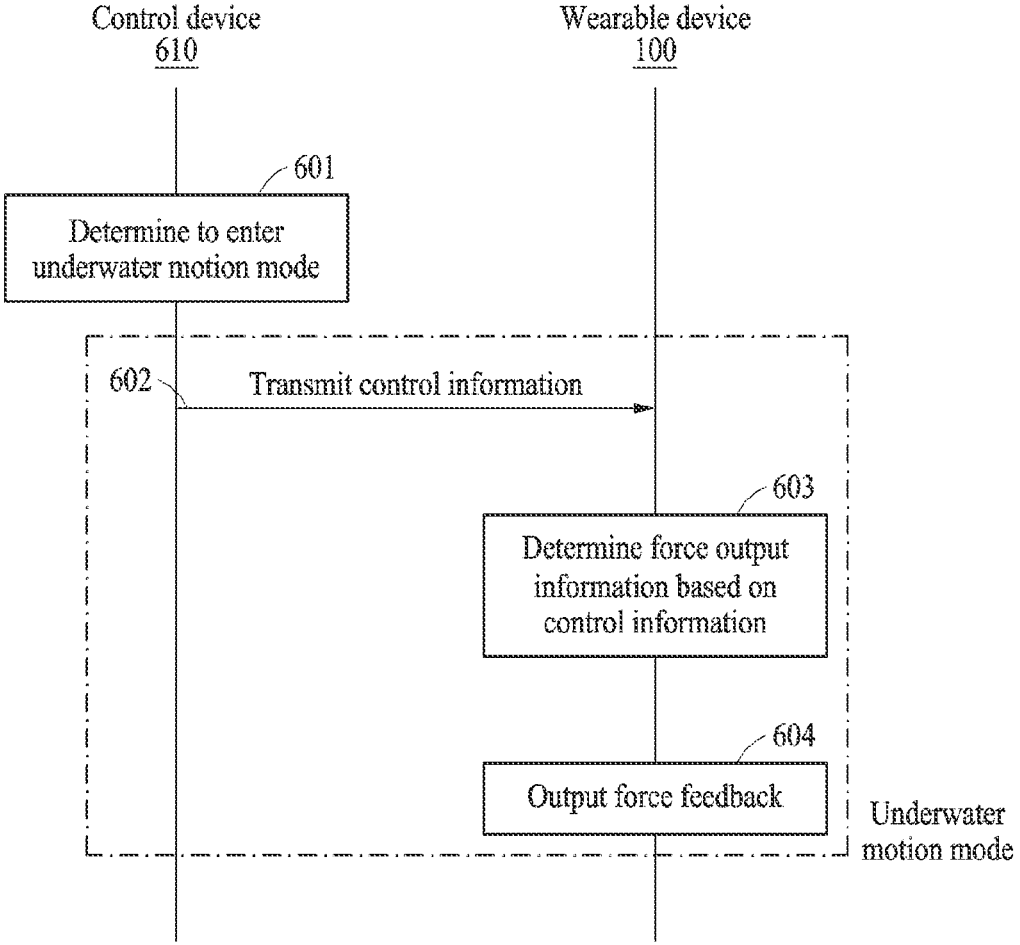
FIG. 6B is a diagram illustrating operations of devices providing an underwater motion mode according to an example embodiment.

FIG. 6B is a diagram illustrating operations of devices providing an underwater motion mode according to an example embodiment.

Referring to FIG. 6B, in operation 601, a control device 610 (e.g., the electronic device 210, the wireless earphones 222, and the smartwatch 224 of FIG. 2) may determine an entry into an underwater motion mode of the wearable device 100. The underwater motion mode may correspond to an aqua mode, be included in the aqua mode, or include the aqua mode. An environment in which a user may virtually experience an underwater motion according to the underwater motion mode may be provided. The underwater motion may indicate that an entire body or a part of the body of the user moves in the water.

The control device 610 may determine the entry into the underwater motion mode according to an input to the control device 610 from the user who desires to enter the underwater motion mode. In a case in which the control device 610 corresponds to the electronic device 210 and/or the smartwatch 224, a button for entering the underwater motion mode may be displayed on the electronic device 210, and the entry into the underwater motion mode may be determined when the user presses the button. In a case in which the control device 610 corresponds to the wireless earphones 222, the entry into the underwater motion mode may be determined by a manipulation (e.g., a multi-touch input) on the wireless earphones 222. The control device 610 may determine to enter the underwater motion mode by itself when there is a need to increase a resistance force by the wearable device 100. When there is a need to increase an exercise intensity of an exercise program using the wearable device 100, the control device 610 may determine to enter the underwater motion mode by itself.

In operation 602, the control device 610 may transmit control information for controlling the wearable device 100 to the wearable device 100. The control device 610 may transmit the control information to the wearable device 100 such that the wearable device 100 may output force feedback that matches such an underwater motion environment. The control information may include, for example, at least one of parameters such as gain $\kappa$ and delay $\Delta t$. The control device 610 may determine the parameter based on at least one of a water depth, a water current direction, and a water current speed of the assumed underwater environment. The gain may correspond to a negative gain $-\kappa$. According to the negative gain $-\kappa$, a resistance force in an opposite direction of a body motion of the user may be generated. The negative gain $-\kappa$ may hinder the body motion of the user. An absolute value of the gain may increase as the water depth increases, and as the water current speed increases while a direction of the motion and the water current direction are opposite to each other.

The wearable device 100 may determine force output information based on the control information received from the control device 610 in operation 603 and output force feedback based on the force output information in operation 604. For example, the wearable device 100 may determine the force output information using the negative gain $-\kappa$. The wearable device 100 may output force feedback based on the determined force output information. In this case, the output force feedback may correspond to the resistance force that provides resistance to the motion of the user. When the user continues doing an underwater motion in a real world, the user may experience a sense of fatigue in lower body muscles. When the user performs an underwater motion in a virtual reality, the wearable device 100 may output force feedback of a resistance force such that the user may experience, in the virtual reality, the sense or such a feeling experienced when the user performs the underwater motion in the real world. The resistance force may be adjusted according to a detailed change in a virtual environment, such as, a change in water depth and water current. Accordingly, the user may experience, in the virtual reality, the feeling that is experienced when performing the underwater motion in the real world.

Figure 6C:
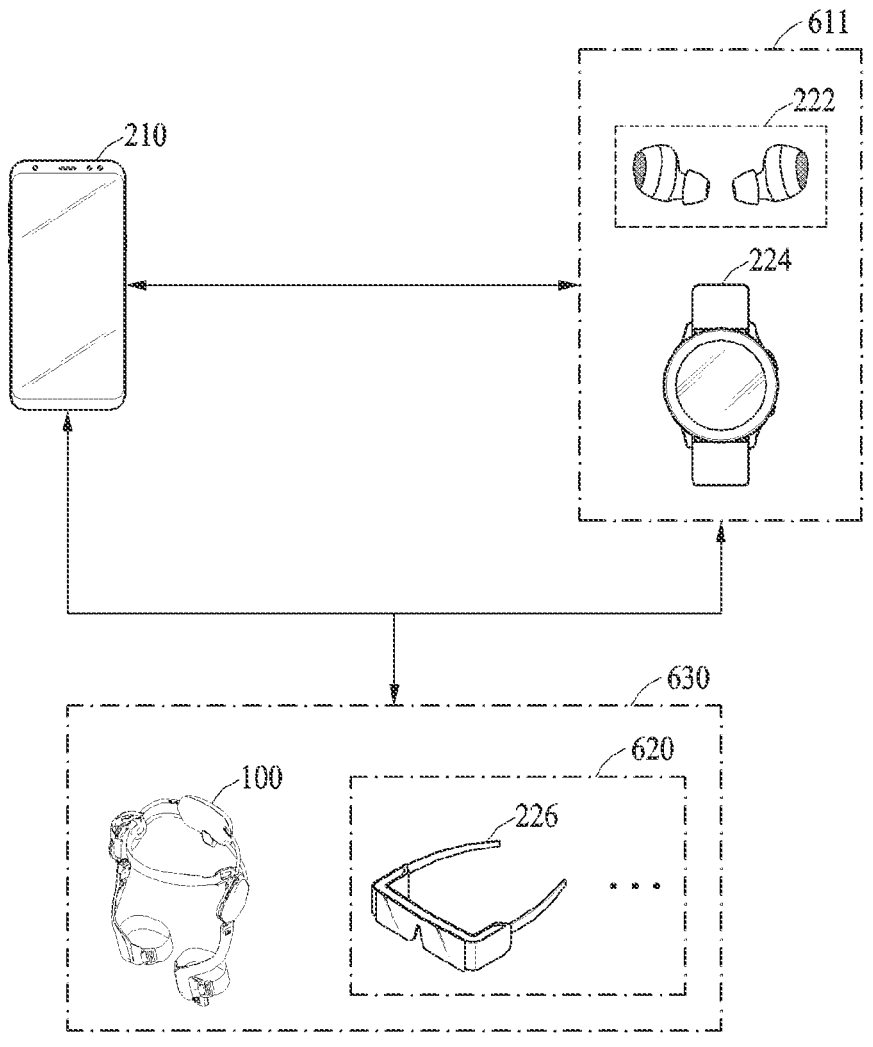
FIG. 6C is a diagram illustrating configurations of devices providing an underwater motion mode according to an example embodiment.

FIG. 6C is a diagram illustrating configurations of devices providing an underwater motion mode according to an example embodiment.

Referring to FIG. 6C, a control command for entering an underwater motion mode may be transmitted from the electronic device 210 and another wearable device 611 to an implementation device 630. The other wearable device 611 may include the wireless earphones 222 and the smartwatch 224 but are not limited thereto. The implementation device 630 may implement the underwater motion mode according to the control command Through the implementation device 630, a user may experience an underwater motion environment in a virtual world. The implementation device 630 may include the wearable device 100 and a display device 620 (e.g., the smart glasses 226 of FIG. 2, a display module 740 of FIG. 7, and a first electronic device 2010 of FIG. 20) but is not limited to.

The electronic device 210 and the other wearable device 611 may correspond to the control device 610 of FIG. 6B. The entry into the underwater motion mode may be determined according to a user input to the electronic device 210 and/or the other wearable device 611, and/or may be determined by itself by the electronic device 210 and/or the other wearable device 611. When the entry into the underwater motion mode is determined through the electronic device 210, the electronic device 210 may transmit the control command to the implementation device 630. When the entry into the underwater motion mode is determined through the other wearable device 611, the other wearable device 611 may directly transmit the control command to the implementation device 630 or indirectly transmit the control command to the implementation device 630 through the electronic device 210.

Figure 6D:
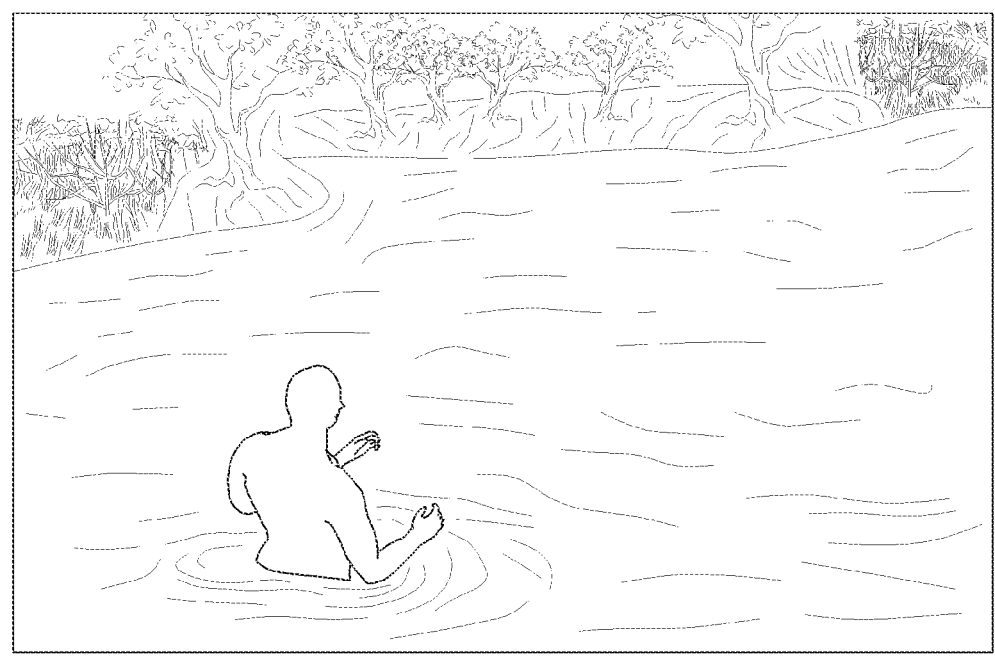
FIG. 6D is a diagram illustrating an example of an underwater motion environment in a virtual reality according to an example embodiment.

FIG. 6D is a diagram illustrating an example of an underwater motion environment in a virtual reality according to an example embodiment.

A display device (e.g., the smart glasses 226 of FIG. 2, the display module 740 of FIG. 7, and the first electronic device 2010 of FIG. 20) may display an underwater motion environment as shown in FIG. 6D.

When a user performs a motion, the display device may output visual feedback to a display, showing as if the user performs an underwater motion. Accordingly, the user may visually feel as if walking in the water.

In addition, when the user enters the underwater motion environment shown in FIG. 6D in a virtual reality, the display device may transmit a negative gain $-\kappa_{water}$ and a delay $\Delta t_{water}$ for delaying an output timing of force feedback to the wearable device 100.

The wearable device 100 may determine force output information that matches the underwater motion environment, using the negative gain $-\kappa_{water}$ and the delay $\Delta t_{water}$.

The wearable device 100 may output force feedback of a resistance force based on the determined force output information. When the user walks in the water in a real world, they may receive resistance from the water. Similarly, when the user performs an underwater motion in the virtual reality, the wearable device 100 may output the force feedback of the resistance force to the user. Accordingly, the user may receive the resistance force when performing an underwater motion in the virtual reality, in a similar way they perform an underwater motion in the real world.

Figure 7:
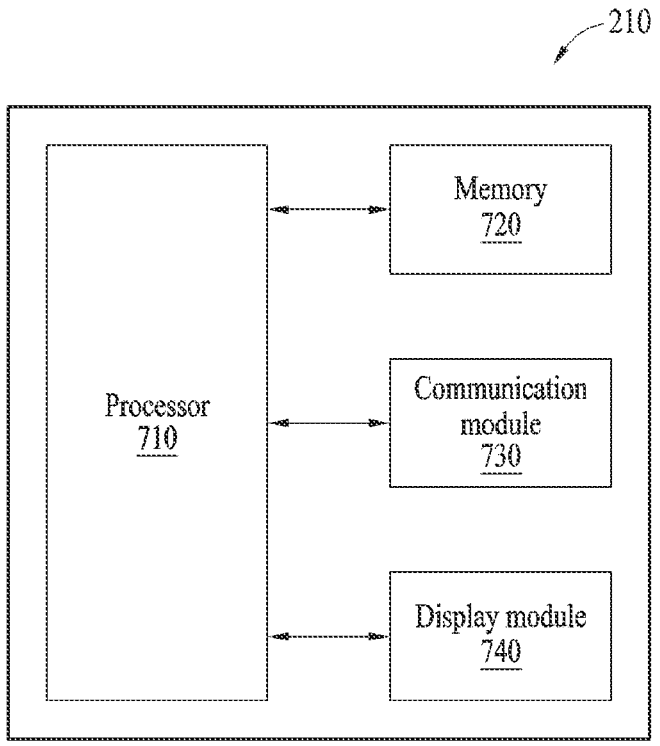
FIG. 7 is a diagram illustrating a configuration of an electronic device according to an example embodiment.

FIG. 7 is a diagram illustrating a configuration of an electronic device according to an example embodiment.

Referring to FIG. 7, the electronic device 210 may include a processor 710, a memory 720, a communication module 730, and a display module 740 comprising a display. In some example embodiments, one or more other components (e.g., an input module and a sensor module) may be added to the electronic device 210.

The processor 710 may control at least one other component (e.g., a hardware or software component) of the electronic device 210 connected, directly or indirectly, to the processor 710 and may perform various data processing or computation. According to an example embodiment, as at least a part of data processing or computation, the processor 710 may store, in the memory 720, instructions or data received from another component (e.g., the communication module 730 comprising communication circuitry), process the instructions or data stored in the memory 720, and store result data in the memory 720.

According to an example embodiment, the processor 710 may include a main processor (e.g., a CPU or an AP) or an auxiliary processor (e.g., a GPU, an NPU, an ISP, a sensor hub processor, or a CP) that is operable independently of, or in conjunction with, the main processor.

The memory 720 may store various data used by at least one component (e.g., the processor 710 or the communication module 730) of the electronic device 210. The data may include, for example, a program (e.g., an application), and input data or output data for an instruction related thereto. The memory 720 may include at least one instruction executable by the processor 710. The memory 720 may include a volatile memory or a non-volatile memory.

The communication module 730 may support establishing a direct (e.g., wired) communication channel or a wireless communication channel between the electronic device 210 and another electronic device (e.g., the wearable device 100, the other wearable device 220, and the server 230), and performing communication via the established communication channel. The communication module 730 may include one or more CPs that are operable independently of the processor 710 (e.g., an AP) and support direct (e.g., wired) communication or wireless communication. According to an example embodiment, the communication module 730 may include a wireless communication module (e.g., a Bluetooth communication module, a cellular communication module, a short-range wireless communication module, or a GNSS communication module) that performs wireless communication, or a wired communication module (e.g., a LAN communication module, or a power line communication (PLC) module). A corresponding one of these communication modules may communicate with another electronic device via a first network (e.g., a short-range communication network, such as, Bluetooth™, Wi-Fi direct, or IrDA) or a second network (e.g., a long-range communication network, such as, a legacy cellular network, a 5G network, a next-generation communication network, the Internet, or a computer network (e.g., a LAN or a WAN)).

The display module 740 may visually provide information to the outside (e.g., a user) of the electronic device 210. The display module 740 may include, for example, a display, a hologram device, or a projector, and control circuitry for controlling a corresponding one of the display, the hologram device, and the projector. For example, the display module 740 may include a touch sensor adapted to sense a touch, or a pressure sensor adapted to measure an intensity of a force generated by the touch.

In an example embodiment, the electronic device 210 may include the communication module 730 configured to communicate with the wearable device 100. The electronic device 210 may include the processor 710. The processor 710 may provide a first exercise program of a first exercise period according to an initial exercise intensity range to a user wearing the wearable device 100. The processor 710 may measure a first posture score of the user while the user is performing the first exercise program. The processor 710 may compare the first posture score to a posture boundary value. The processor 710 may set a personal exercise intensity range of the user based on a comparison result obtained by the comparing. The processor 710 may provide a second exercise program of a second exercise period according to the personal exercise intensity range.

The posture boundary value may include an upper boundary value and a lower boundary value. The personal exercise intensity range may be determined by an upper intensity value and a lower intensity value.

To set a personal exercise intensity, the processor 710 may set, as the lower intensity value, a first current exercise intensity at a first time point when the first posture score and the upper boundary value cross each other at the first time point according to a change in a current exercise intensity of the first exercise program. To set the personal exercise intensity, the processor 710 may set, as the upper intensity value, a second current exercise intensity at a second time point when the first posture score and the lower boundary value cross each other at the second time point according to a change in the current exercise intensity of the first exercise program.

To provide at least one of the first exercise program or the second exercise program, the processor 710 may display a virtual object on a display device and induce the user to perform a motion. To provide at least one of the first exercise program or the second exercise program, the processor 710 may generate an exercise load for the motion of the user through the wearable device 100.

At least a portion of the initial exercise intensity range and the personal exercise intensity range may be set according to a first intensity factor associated with the virtual object and a second intensity factor associated with the exercise load.

The first intensity factor may be set based on at least one of a first sub-intensity factor associated with a distance between a center of weight of the user and the virtual object, a second sub-intensity factor associated with a distance between neighboring virtual objects including the virtual object, a third sub-intensity factor associated with a height of the virtual object, a fourth sub-intensity factor associated with a size of the virtual object, or a fifth sub-intensity factor associated with a moving speed of the virtual object.

At least one of the first posture score or the second posture score may be determined based on a first posture factor associated with posture stability of the user and a second posture factor associated with a distance between the user and the virtual object.

To provide the second exercise program, the processor 710 may measure the second posture score of the user while the user is performing the second exercise program. To provide the second exercise program, when the second posture score is out of a control margin of the posture boundary value, the processor 710 may adjust a current exercise intensity of the second exercise program.

The posture boundary value may include an upper boundary value and a lower boundary value. For the upper boundary value, a first upper control margin and a first lower control margin may be set. The personal exercise intensity range may be determined by the upper intensity value and the lower intensity value. To adjust the current exercise intensity of the second exercise program, when the second posture score exceeds the first upper control margin, the processor 710 may increase the current exercise intensity of the second exercise program. The processor 710 may stop increasing the current exercise intensity when the second posture score becomes less than the first lower control margin as the current exercise intensity increases.

For the lower boundary value, a second upper control margin and a second lower control margin may be set. To adjust the current exercise intensity of the second exercise program, when the second posture score is less than the second lower control margin, the processor 710 may decrease the current exercise intensity of the second exercise program. To adjust the current exercise intensity of the second exercise program, the processor 710 may stop decreasing the current exercise intensity when the second posture score exceeds the second upper control margin as the current exercise intensity decreases.

To adjust the current exercise intensity of the second exercise program, the processor 710 may adjust in real time the current exercise intensity of the second exercise program as the second posture score is out of the control margin of the posture boundary value.

The personal exercise intensity range may include a left intensity range for a left body part of the user and a right intensity range for a right body part of the user. The provision of the second exercise program and the measurement of the second posture score may be performed independently for the left intensity range and the right intensity range.

FIG. 8 is a flowchart illustrating a control method according to an example embodiment. Referring to FIG. 8, in operation 810, a first exercise program of a first exercise period may be provided to a user wearing a wearable device according to an initial exercise intensity range. The first exercise period may correspond to a warm-up exercise period. In operation 820, a first posture score of the user may be measured while the user is performing the first exercise program. In operation 830, the first posture score may be compared to a posture boundary value. In operation 840, a personal exercise intensity range of the user may be set based on a comparison result obtained by the comparing. In operation 850, a second exercise program of a second exercise period may be provided according to the personal exercise intensity range. The second exercise program may correspond to a personalized exercise program.

Operation 850 may include measuring a second posture score of the user while the user is performing the second exercise program. Operation 850 may include adjusting a current exercise intensity of the second exercise program when the second posture score is out of a control margin of the posture boundary value.

The posture boundary value may include an upper boundary value and a lower boundary value. The personal exercise intensity range may be determined by an upper intensity value and a lower intensity value. Operation 840 may include setting, as the lower intensity value, a first current exercise intensity at a first time point when the first posture score and the upper boundary value cross each other at the first time point by a change in a current exercise intensity of the first exercise program. Operation 840 may include setting, as the upper intensity value, a second current exercise intensity at a second time point when the first posture score and the lower boundary value cross at the second time point by a change in the current exercise intensity of the first exercise program.

An exercise program using the wearable device may be provided through virtual content. The virtual content may include a virtual underwater environment and a virtual object. For example, a virtual object may be provided in the virtual underwater environment, a virtual object may be provided in a virtual ground environment, or the virtual underwater environment without a virtual object may be provided. At least a part of operations 810 and 850 may include displaying virtual content (e.g., a virtual object) on the display device to induce the user to perform a motion. At least a part of operations 810 and 850 may include generating an exercise load for the motion of the user through the wearable device.

The posture boundary value may include an upper boundary value and a lower boundary value. For the upper boundary value, a first upper control margin and a first lower control margin may be set. The personal exercise intensity range may be determined by an upper intensity value and a lower intensity value. An operation of adjusting a current exercise intensity of the second exercise program may include increasing the current exercise intensity of the second exercise program when the second posture score exceeds the first upper control margin. The operation of adjusting the current exercise intensity of the second exercise program may include stopping increasing the current exercise intensity when the second posture score becomes less than the first lower control margin as the current exercise intensity increases.

Figure 9:
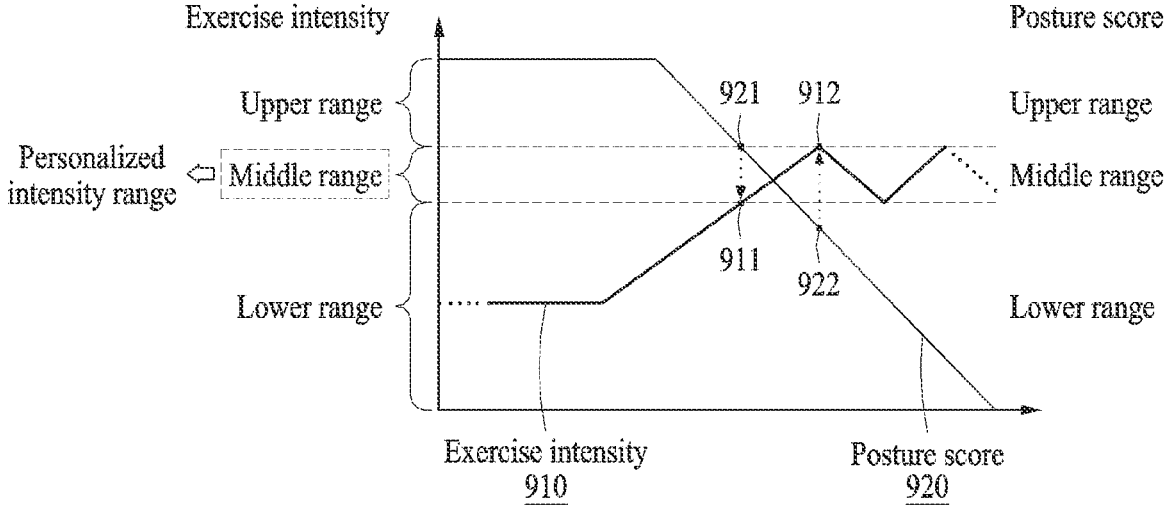
FIG. 9 is a diagram illustrating an example of a change in exercise intensity and posture score in a warm-up exercise period according to an example embodiment.

FIG. 9 is a diagram illustrating an example of a change in exercise intensity and posture score in a warm-up exercise period according to an example embodiment. Referring to FIG. 9, a posture score 920 according to a change in an exercise intensity 910 of a warm-up exercise in a warm-up exercise period may be measured. A personalized intensity range for a user may be set based on the posture score 920 according to the change in the exercise intensity 910. The user may perform a motion induced by virtual content (e.g., a virtual object) of a display device (e.g., the smart glasses 226 of FIG. 2, the display module 740 of FIG. 7, and the first electronic device 2010 of FIG. 20) with a wearable device (e.g., the wearable device 100) worn on the user. The wearable device 100 may generate an exercise load for the motion of the user. The exercise intensity 910 may be adjusted according to a first intensity factor associated with the virtual object and a second intensity factor associated with the exercise load.

According to an example embodiment, the exercise intensity 910 may be classified into an upper range, a middle range, and a lower range according to an individual exercise ability of a user. However, the exercise intensity 910 is not limited to the foregoing classification. In the warm-up exercise period, the exercise intensity 910 of the warm-up exercise may be adjusted. The upper range, the middle range, and the lower range of the exercise intensity 910 according to the exercise ability of the user may be set based on the posture score 920 of the user according to the change in the exercise intensity 910. An intensity at a level that allows the middle range of the posture score 920 to be maintained may be set as the middle range of the exercise intensity 910. The middle range of posture score 920 may be referred to as an optimal posture range.

The posture score 920 may be classified into an upper range, a middle range, and a lower range according to a posture boundary value. However, the posture score 920 is not limited to the foregoing classification. The posture boundary value may include an upper boundary value and a lower boundary value. The upper boundary value may divide the upper range and the middle range. The lower boundary value may divide the middle range and the lower range. The posture boundary value may be determined in advance based on clinical data. For example, a range of appropriate exercise postures in which an appropriate exercise effect is achieved without side effects when a user performs an exercise program may be determined in advance. Such a range of appropriate exercise postures may be set as the middle range. For example, as the exercise program progresses, the posture boundary value may be optimized according to exercise data of the user. In the example of FIG. 9, the middle range may be set according to an upper boundary value 921 and a lower boundary value 922 of the posture boundary value.

According to an example embodiment, the exercise intensity 910 in the warm-up exercise period may gradually increase from an initial value. For example, the initial value may be set according to a previous exercise result of the user or may be set as a previously given value. While the exercise intensity 910 is adjusted, the posture score 920 may be measured. As the exercise intensity 910 changes, the posture score 920 and the upper boundary value 921 of the posture boundary value may cross each other at a first time point. A first exercise intensity 911 at the first time point may be set as a lower intensity value of the middle range of the exercise intensity 910. At a second time point, the posture score 920 and the lower boundary value 922 of the posture boundary value may cross. A second exercise intensity 912 at the second time point may be set as an upper intensity value of the exercise intensity 910. The middle range of the exercise intensity 910 that is formed by the upper intensity value of the first exercise intensity 911 and the lower intensity value of the second exercise intensity 912 may be set as the personalized intensity range for the user. The personalized intensity range may also be referred to herein as a personal exercise intensity range. With respect to the middle range of the exercise intensity 910, the upper range may correspond to high intensity for the user, and the lower range may correspond to low intensity for the user.

Figure 10:
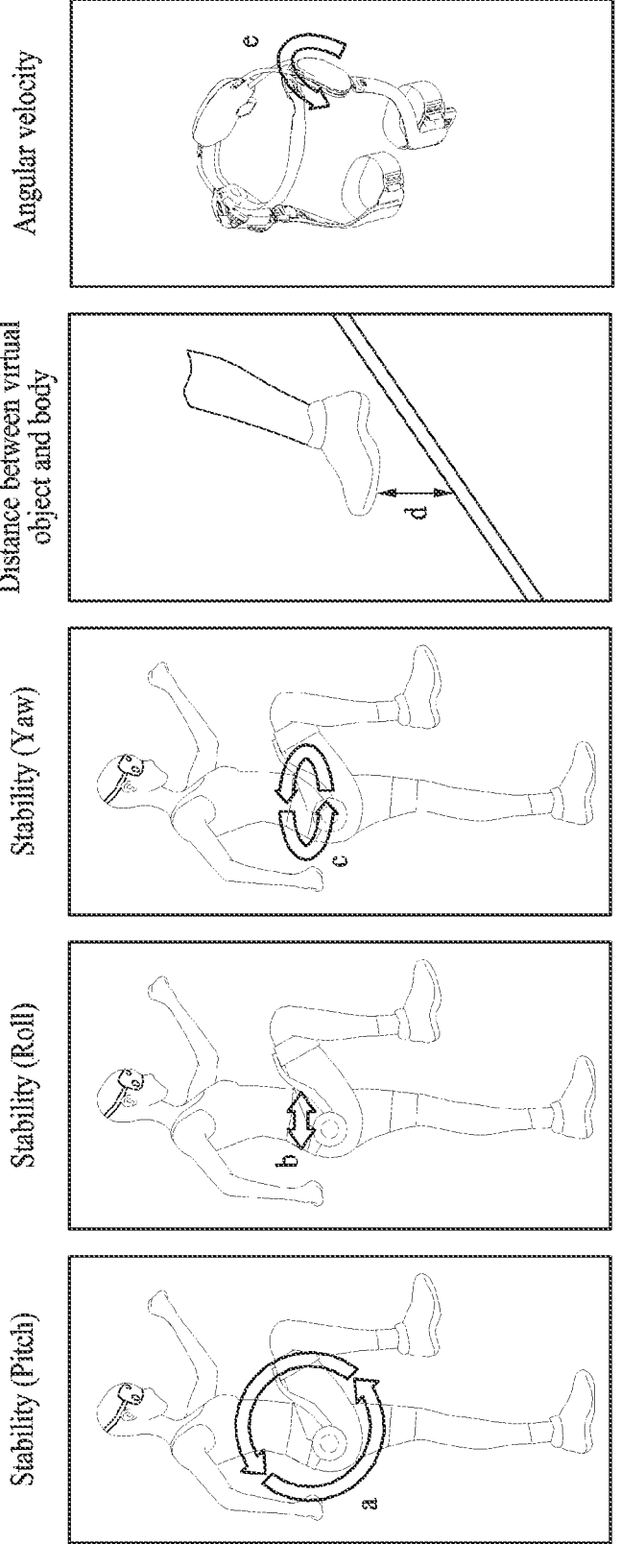
FIG. 10 is a diagram illustrating an example of factors used to measure a posture score according to an example embodiment.

FIG. 10 is a diagram illustrating an example of factors used to measure a posture score according to an example embodiment. The posture score may be measured based on an assessment factor specific to a posture required by an exercise program. For example, the factors to be described below with reference to FIG. 10 may be used to measure a posture score associated with a knee-up exercise.

According to an example embodiment, the posture score may be measured according to a posture factor associated with posture stability of a user. A higher posture score may be evaluated when the user takes a stable posture without unnecessary movement while performing a knee-up. The posture factor associated with posture stability may be measured using an inertial sensor (e.g., the IMU 135 of the wearable device 100 or an IMU of the smart glasses 226).

The posture factor associated with posture stability may include a pitch-related posture factor a. The posture factor a may indicate whether the pelvis tilts forward/backward (front/back) during an exercise. According to an example embodiment, a score range of the posture factor a may be determined in advance based on clinical data. For example, the posture factor a of 2° (backward) to 8° (forward) may be evaluated as an upper range. The posture factor a of 0° to 2° (backward) and 8° to 10° (forward) may be evaluated as a middle range. The posture factor a in other ranges may be evaluated as a lower range.

The posture factor associated with posture stability may include a roll-related posture factor b. The posture factor b may indicate whether the center of the pelvis is parallel to the ground. According to an example embodiment, a score range of the posture factor b may be determined in advance based on clinical data. For example, the posture factor b of 0° to 10° may be evaluated as an upper range. The posture factor b of 10° to 20° may be evaluated as a middle range. The posture factor b in other ranges may be evaluated as a lower range.

The posture factor associated with posture stability may include a yaw-related posture factor c. The posture factor c may indicate whether the pelvis rotates during a motion. According to an example embodiment, a score range of the posture factor c may be determined in advance based on clinical data. For example, the posture factor c of 0° to 10° may be evaluated as an upper range. The posture factor c of 10° to 20° may be evaluated as a middle range. The posture factor c in other ranges may be evaluated as a lower range.

According to an example embodiment, the posture score may be measured according to a posture factor d associated with a distance between the user and virtual content (e.g., a virtual object). When the user steps over (or crosses) the virtual object through the knee-up, the higher the posture factor d is, the higher the posture score may be evaluated. The posture factor d may be measured using a motion recognition sensor (e.g., the electronic device 210, or a camera, a time of flight (TOF) sensor, or an ultrasonic sensor of the smart glasses 226).

According to an example embodiment, the posture score may be measured according to a posture factor e associated with an angular velocity. When the posture factor e decreases during the knee-up, the posture score may be evaluated as low. The posture factor e may be measured using an angle sensor (e.g., the angle sensor 125). In addition, sensor data (e.g., electromyography data) may be used as another reference for a posture factor.

According to the example of FIG. 10, the posture score may be determined as expressed by Equation 1 below.

$$S=a\times W_4+b\times W_5+c\times W_6+d\times W_7+e\times W_8+f \qquad \text{[Equation 1]}$$

In Equation 1, S denotes the posture score, a denotes the posture factor a, b denotes the posture factor b, c denotes the posture factor c, d denotes the posture factor d, and e denotes the posture factor e. $W_4$, $W_5$, $W_6$, $W_7$, and $W_8$ denote weights. f denotes another posture factor.

Figure 11:
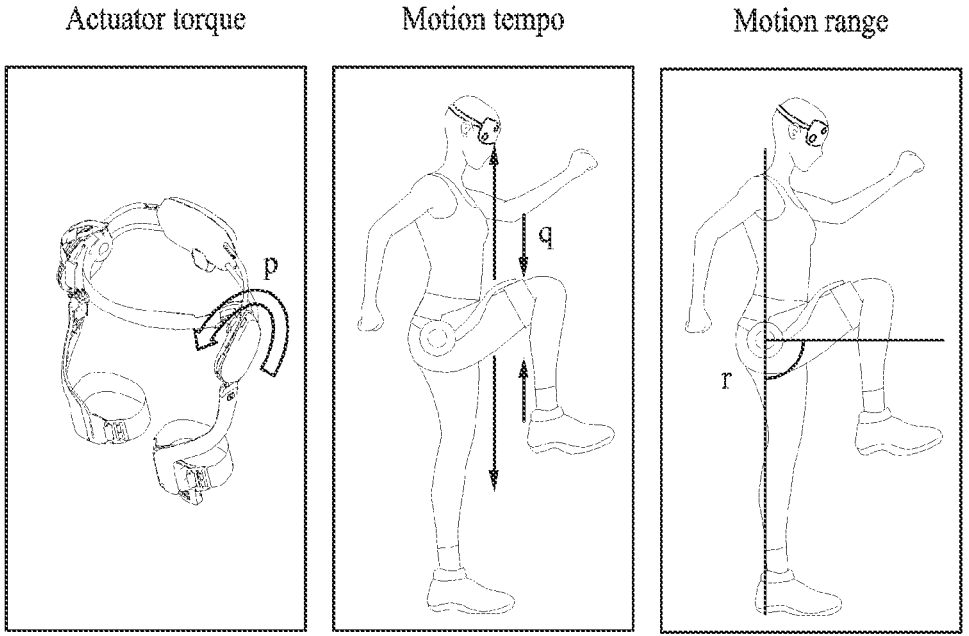
FIG. 11 is a diagram illustrating an example of factors used to adjust an exercise intensity according to an example embodiment.

FIG. 11 is a diagram illustrating an example of factors used to adjust an exercise intensity according to an example embodiment. Referring to FIG. 11, an exercise intensity may be set according to an intensity factor p associated with an exercise load. For example, the exercise load may be adjusted by an actuator torque of a driving module (e.g., the driving module 120, the driving module 35, the driving module 45, the driving module 530, or the driving module 530-1) of a wearable device (e.g., the wearable device 100). The driving module may generate an exercise load in an opposite direction of a body's movement direction of the user.

The exercise intensity may be adjusted through virtual content. The exercise intensity may be set according to intensity factors q and r associated with a virtual object. The intensity factor q may indicate a motion tempo. For example, a situation requiring fast stepping over virtual objects may increase a motion tempo of the user. The intensity factor r may indicate a motion range. The motion range may correspond to an angle between both legs. For example, a situation requiring stepping over a high virtual object may increase a motion range of the user.

According to the example of FIG. 11, the exercise intensity may be determined as expressed by Equation 2 below.

$$I=p\times W_1+q\times W_2+r\times W_3 \qquad \text{[Equation 2]}$$

In Equation 2, I denotes the exercise intensity, p denotes the intensity factor p, q denotes the intensity factor q, and r denotes the intensity factor r. $W_1$, $W_2$, and $W_3$ denote weights.

Figure 12:
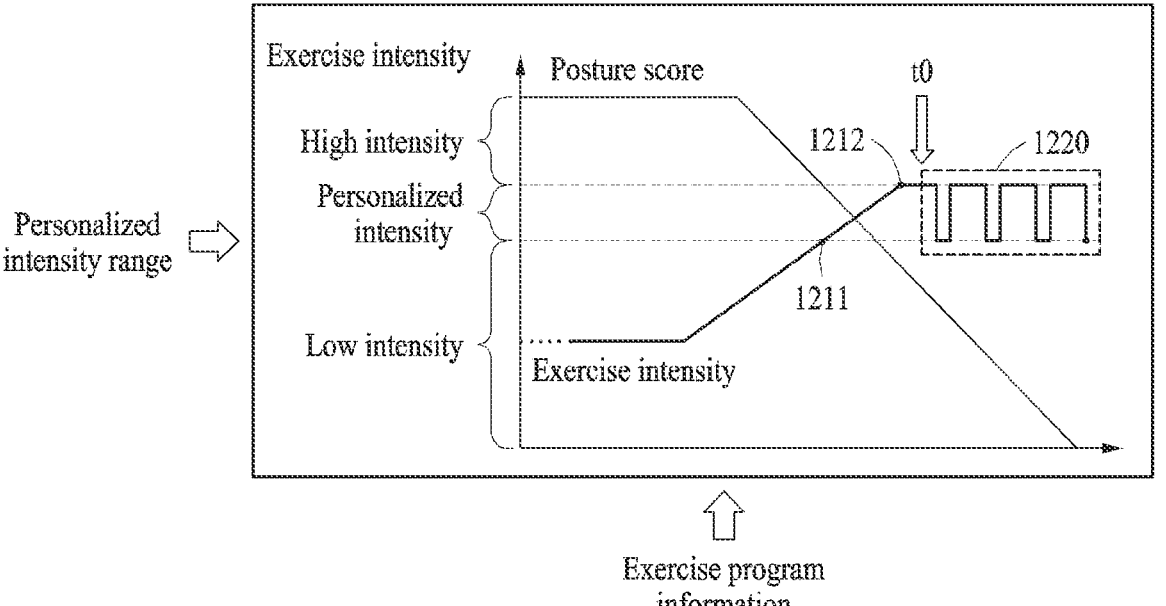
FIG. 12 is a diagram illustrating an example of a change in exercise intensity and posture score in a warm-up exercise period and a personalized exercise period according to an example embodiment.

FIG. 12 is a diagram illustrating an example of a change in exercise intensity and posture score in a warm-up exercise period and a personalized exercise period according to an example embodiment. Referring to FIG. 12, a personalized exercise program may be provided based on a personalized intensity range and exercise program information. Through the warm-up exercise period, a lower intensity value 1211 and an upper intensity value 1212 of the personalized intensity range may be set. The exercise program information may include an exercise type. The exercise type of the exercise program information may be selected by a user or recommended by an exercise application. FIG. 12 shows an example of interval training, but examples are not limited thereto. The personalized exercise program may start at a time t0. When the personalized exercise program starts, an exercise program of a type according to the exercise program information may be provided during a personalized exercise period 1220. An intensity of the exercise program of the type may be set according to a personalized intensity range of the user. In the example of FIG. 12, during the personalized exercise period 1220, an interval training program according to the lower intensity value 1211 and the upper intensity value 1212 may be provided. Such a personalized exercise may prevent or reduce injuries and maximize or improve exercise effects.

Figure 13:
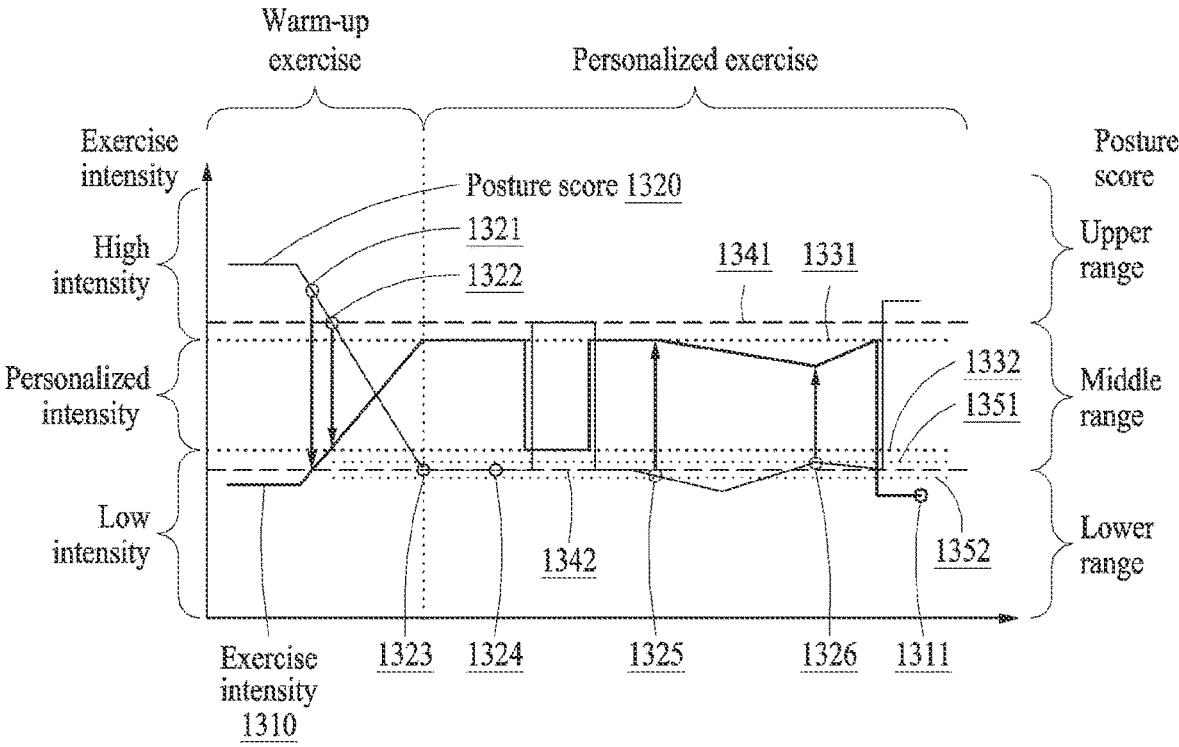
FIG. 13 is a diagram illustrating an example of adjusting in real time an exercise intensity in a personalized exercise period according to an example embodiment.

FIG. 13 is a diagram illustrating an example of adjusting in real time an exercise intensity in a personalized exercise period according to an example embodiment. Referring to FIG. 13, a posture score 1320 according to an exercise intensity 1310 may be measured during a warm-up exercise period. For example, a change in the posture score 1320 by an increase in the exercise intensity 1310 may be measured. A first posture score 1321 is higher than an upper boundary value 1341 of a middle range of the posture score 1320, and thus the exercise intensity 1310 may increase further. A second posture score 1322 is equal to the upper boundary value 1341, and thus an exercise intensity at a time point when the second posture score 1322 is measured may be determined as a lower intensity value 1332 of a personalized intensity range. A third posture score 1323 is equal to a lower boundary value 1342 of the middle range of the posture score 1320, and thus an exercise intensity at a time point when the third posture score 1323 is measured may be determined as an upper intensity value 1331 of the personalized intensity range.

As the personalized intensity range is determined by the upper intensity value 1331 and the lower intensity value 1332, the warm-up exercise period may end, and the personalized exercise period may start. In the personalized exercise period, an exercise of a type according to exercise program information may be provided within a personal exercise intensity range according to personalized intensity information. During the personalized exercise period, the exercise intensity 1310 according to the personalized exercise intensity range (or a personal exercise intensity range) may be adjusted, and the posture score 1320 according to the adjustment of the exercise intensity 1310 may be measured.

In the personalized exercise period, the exercise intensity 1310 may be controlled or adjusted in real time according to the posture score 1320. To adjust the exercise intensity 1310, control margins 1351 and 1352 may be used. Adjusting the exercise intensity 1310 each time the posture score 1320 is out of the upper boundary value 1341 and/or the lower boundary value 1342 may be inefficient in terms of an amount of computation or exercise effects. For example, when the posture score 1320 is less than the lower control margin 1352, the exercise intensity 1310 may decrease. When the posture score 1320 exceeds the upper control margin 1351 as the exercise intensity 1310 decreases, decreasing the exercise intensity 1310 may stop. Although the control margins 1351 and 1352 of the lower boundary value 1342 are shown in FIG. 13, control margins may also be set for the upper boundary value 1341. For example, when the posture score 1320 exceeds an upper control margin of the upper boundary value 1341, the current exercise intensity 1310 may increase. When the posture score 1320 becomes less than a lower control margin of the upper boundary value 1341 as the exercise intensity 1310 increases, increasing the exercise intensity 1310 may stop.

A fourth posture score 1324 may be measured according to an exercise performed by the user in the personalized exercise period. The fourth posture score 1324 may be equal to the lower boundary value 1342. The fourth posture score 1324 is greater than the lower control margin 1352, and thus real-time control of the exercise intensity 1310 may not be performed. A fifth posture score 1325 may be equal to the lower control margin 1352. The posture score 1320 falls below the lower control margin 1352 after the fifth posture score 1325 is measured, and thus the exercise intensity 1310 may decrease. A sixth posture score 1326 may be equal to the upper control margin 1351. The posture score 1320 exceeds the upper control margin 1351 after the sixth posture score 1326 is measured, and thus the exercise intensity 1310 may stop decreasing. The exercise intensity 1310 may be maintained or increased again. As shown in FIG. 13, the exercise intensity 1310 may be restored to the upper intensity value 1331. As the personalized exercise period ends, the exercise intensity 1310 may be minimized or reduced to be the first exercise intensity 1311.

Figure 14A:
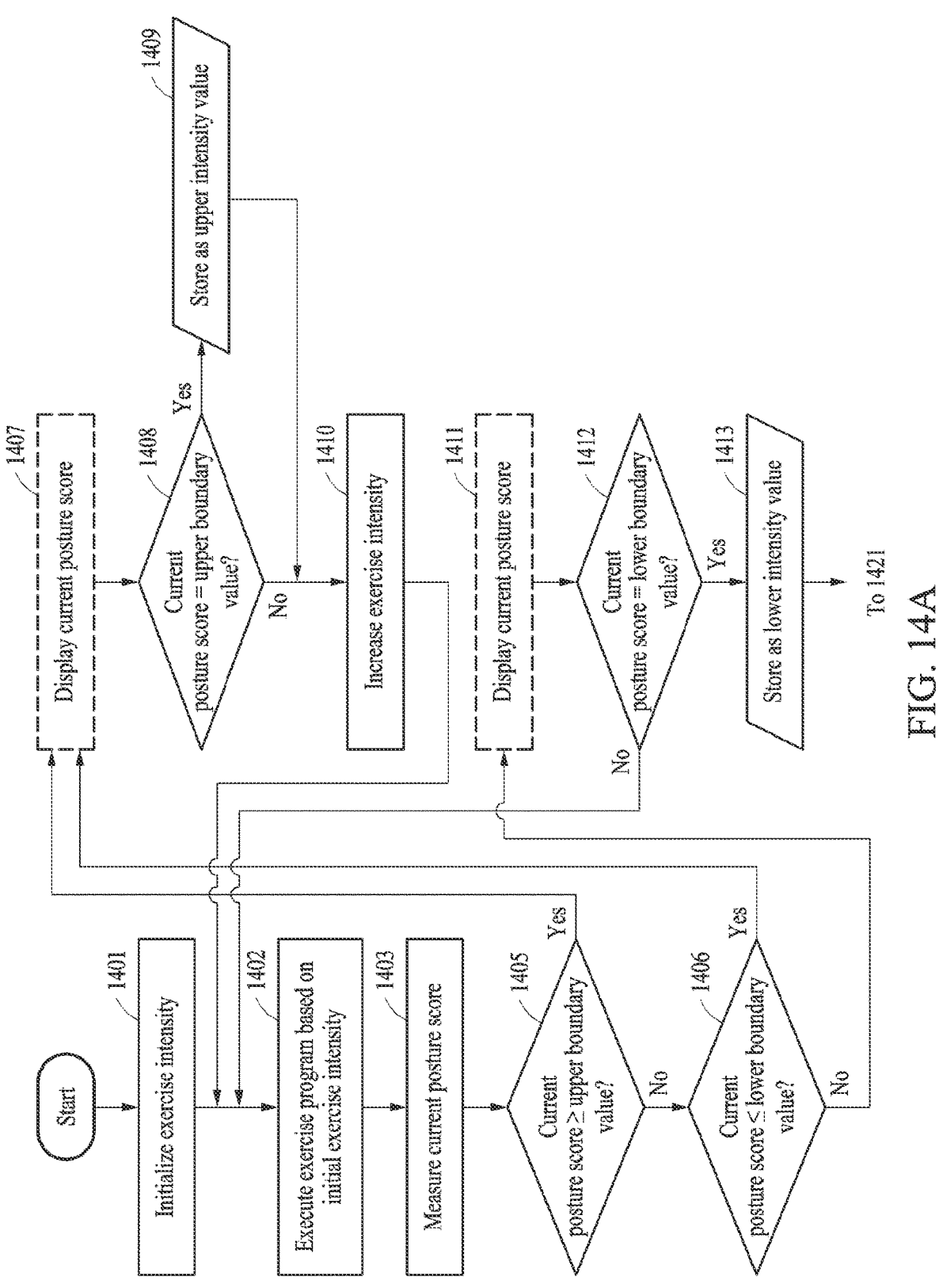
FIGS. 14A and 14B are flowcharts illustrating detailed examples of a control method according to an example embodiment.
Figure 14B:
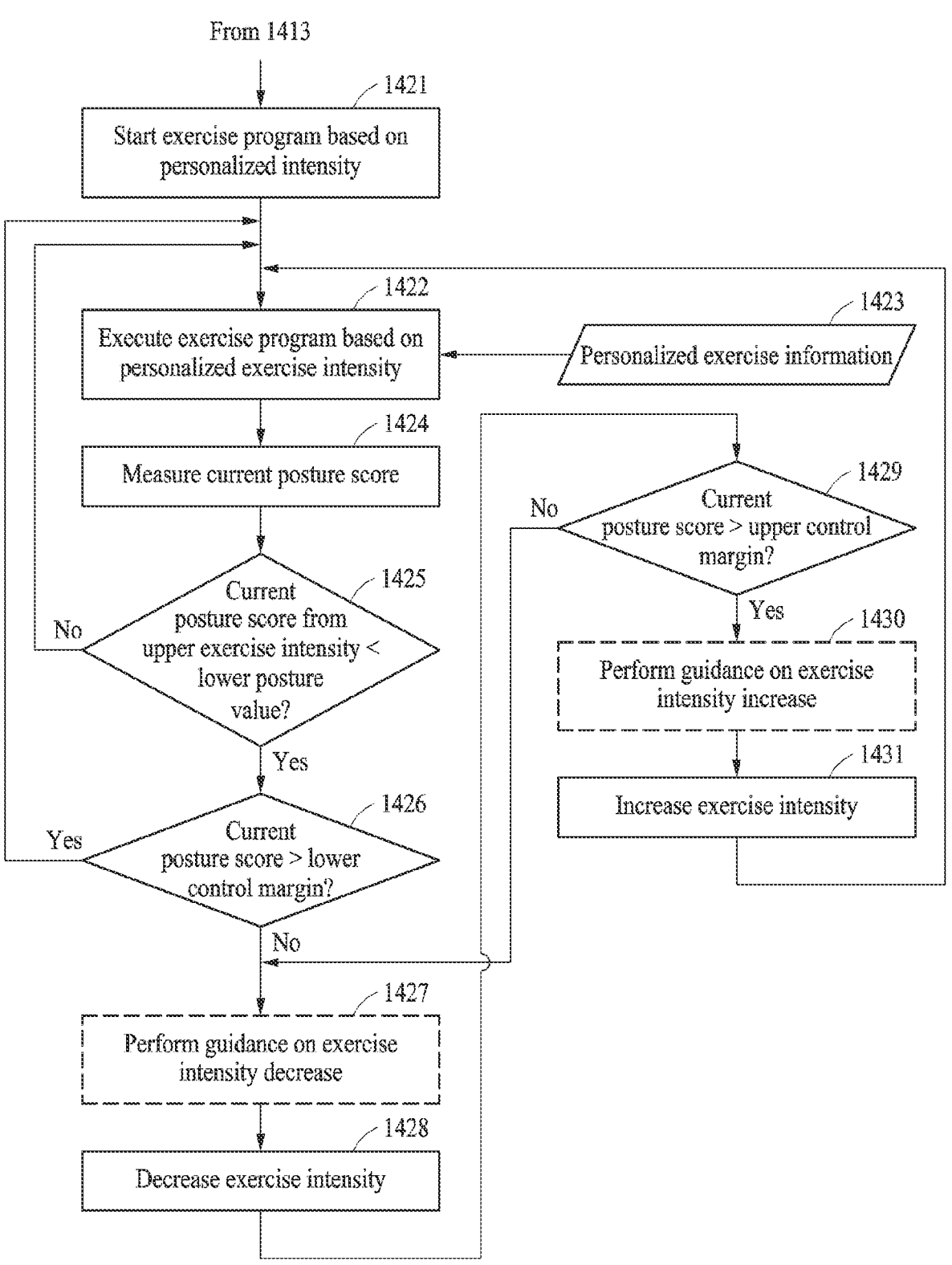

FIGS. 14A and 14B are flowcharts illustrating detailed examples of a control method according to an example embodiment. Referring to FIG. 14A, in operation 1401, an exercise intensity may be initialized to an initial value. For example, the initial value may be set according to a previous exercise result of a user or may be set as a previously given value. In operation 1402, an exercise program may be executed based on the initial exercise intensity. The exercise intensity may be set according to at least a part of a first intensity factor associated with a virtual object and a second intensity factor associated with an exercise load. In operation 1403, a current posture score may be measured. The current posture score may be measured according to at least some of a posture factor associated with stability, a posture factor associated with a distance between the user and the virtual object, a posture factor associated with an angular velocity, and other posture factors.

In operation 1405, the current posture score and an upper boundary value of an optimal posture range may be compared. When the current posture score is greater than or equal to the upper boundary value, operation 1407 may be performed. When the current posture score is less than the upper boundary value, operation 1406 may be performed. In operation 1406, the current posture score and a lower boundary value of the optimal posture range may be compared. When the current posture score is less than or equal to the lower boundary value, operation 1407 may be performed. When the current posture score is greater than the lower boundary value, operation 1411 may be performed.

In operation 1407, the current posture score may be displayed. According to an example embodiment, the current posture score may be displayed through an exercise application of an electronic device (e.g., the electronic device 210). When the current posture score is equal to the upper boundary value in operation 1408, the current posture score may be stored as an upper intensity value of a personal exercise intensity range in operation 1409. When the current posture score is not equal to the upper boundary value in operation 1408, the exercise intensity may increase in operation 1410. In operation 1411, the current posture score may be displayed. When the current posture score is equal to the lower boundary value in operation 1412, the current exercise intensity may be stored as a lower intensity value of the personal exercise intensity range in operation 1413.

Referring to FIG. 14B, in operation 1421, an exercise program may start based on a personalized intensity. In a personalized exercise program, an exercise intensity may be controlled (or adjusted) in real time according to a posture score. In operation 1422, the exercise program may start based on the personalized intensity. The exercise program may be set based on personalized exercise information 1423. The personalized exercise information 1423 may include a personalized intensity range and/or exercise program information. "Based on" as used herein covers based at least on.

The posture score may be measured at 1424. In operation 1425, when the exercise program is performed at an upper exercise intensity of the personalized intensity range, whether a current posture score is less than a lower boundary value of an optimal posture range may be checked. When the current posture score is less than the lower boundary value, operation 1426 may be performed. In operation 1426, whether the current posture score is greater than a lower control margin of the lower boundary value may be checked. When the current posture score is less than the lower control margin, operation 1427 may be performed. In operation 1427, decreasing the exercise intensity may be guided. According to an example embodiment, such an exercise intensity decrease guidance may be displayed through an exercise application of an electronic device (e.g., the electronic device 210). In operation 1428, the exercise intensity may decrease.

In operation 1429, whether the current posture score is greater than an upper control margin of the lower boundary value may be checked. When the current posture score is greater than the upper control margin, operation 1430 may be performed. In operation 1430, increasing the exercise intensity may be guided. According to an example embodiment, such an exercise intensity increase guidance may be displayed through the exercise application of the electronic device (e.g., the electronic device 210). In operation 1431, the exercise intensity may increase. As the exercise intensity increases, virtual content (e.g., a virtual underwater environment and/or a virtual object) may change. For example, a change in the underwater environment may be provided through a display device (e.g., the smart glass 226 of FIG. 2, the display module 740 of FIG. 7, or the first electronic device 2010 of FIG. 20). For example, a situation in which the body of the user is further sunk under water as the depth of the water deepens, and/or a situation in which a water current that gives resistance to a movement of the user becomes faster may be provided.

Figure 15:
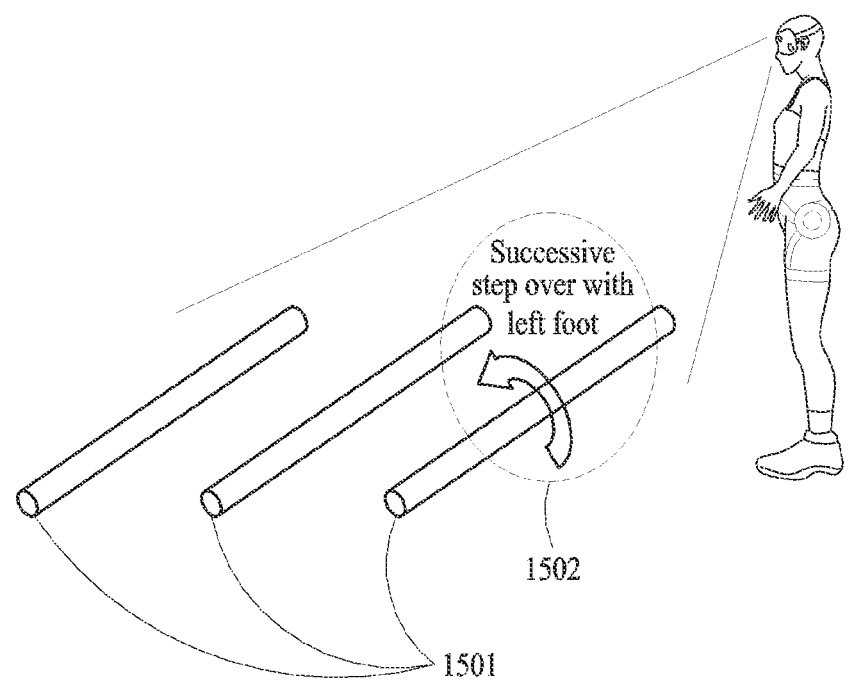
FIG. 15 is a diagram illustrating an example configuration of a virtual screen according to an example embodiment.

FIG. 15 is a diagram illustrating an example configuration of a virtual screen according to an example embodiment. Referring to FIG. 15, a virtual screen may include virtual objects 1501 and an exercise guidance message 1502. According to an example embodiment, the virtual objects 1501 may correspond to obstacles. A user may successively step over the virtual objects 1501 with their left foot according to the exercise guidance message 1502. As shown in FIG. 15, the virtual screen may be provided through smart glasses (e.g., the smart glasses 226). The user may perform an exercise program while stepping over the virtual objects 1501 observed through the smart glasses. When the body of the user touches the virtual objects 1501, a wearable device (e.g., the wearable device 100) may vibrate or a visual effect representing such a collision may be provided around the virtual objects 1501. FIG. 15 shows an example of a knee-up exercise, but examples are not limited thereto, and various exercise programs may be provided.

Figure 16A:
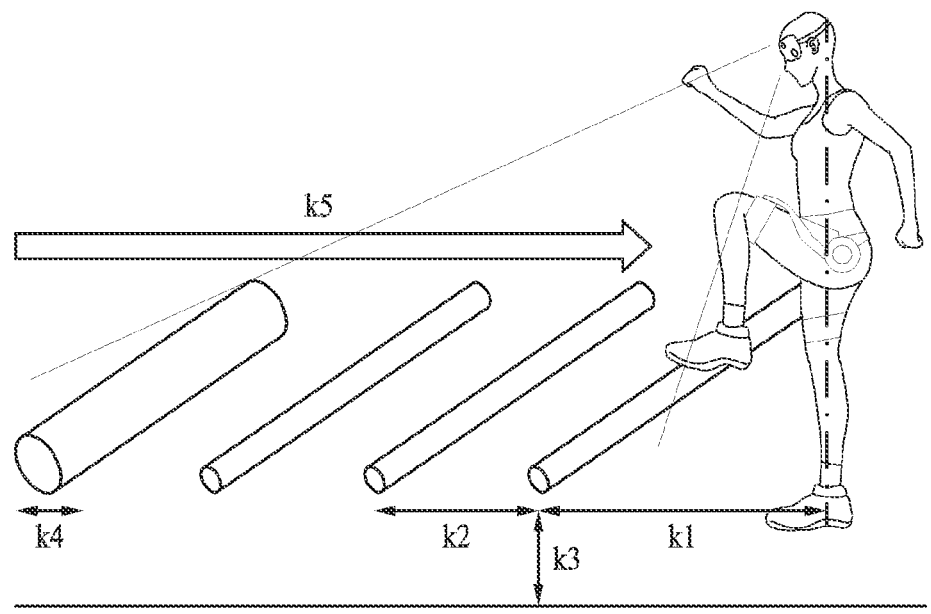
FIG. 16A is a diagram illustrating an example of exercise intensity factors of a virtual object according to an example embodiment.

FIG. 16A is a diagram illustrating an example of exercise intensity factors of a virtual object according to an example embodiment. Referring to FIG. 16A, an exercise intensity factor associated with a virtual object may include at least one of an intensity factor k1 associated with a distance between a center of weight of a user and the virtual object, an intensity factor k2 associated with a distance between neighboring virtual objects including the virtual object, an intensity factor k3 associated with a height of the virtual object, an intensity factor k4 associated with a size of the virtual object, or an intensity factor k5 associated with a moving speed of the virtual object. The intensity factor k4 may include a width of the virtual object.

According to the example of FIG. 16A, the exercise intensity associated with the virtual object may be determined as expressed by Equation 3 below.

$$V = k1 \times W_1 + k2 \times W_2 + k3 \times W_3 + k4 \times W_4 + k5 \times W_5 + k6 \qquad \text{[Equation 3]}$$

In Equation 3, V denotes the exercise intensity, k1 denotes the intensity factor k1, k2 denotes the intensity factor k2, k3 denotes the intensity factor k3, k4 denotes the intensity factor k4, and k5 denotes the intensity factor k5. $W_1$, $W_2$, $W_3$, $W_4$, and $W_5$ denote weights. k6 denotes a constant term according to other factors.

Figure 16B:
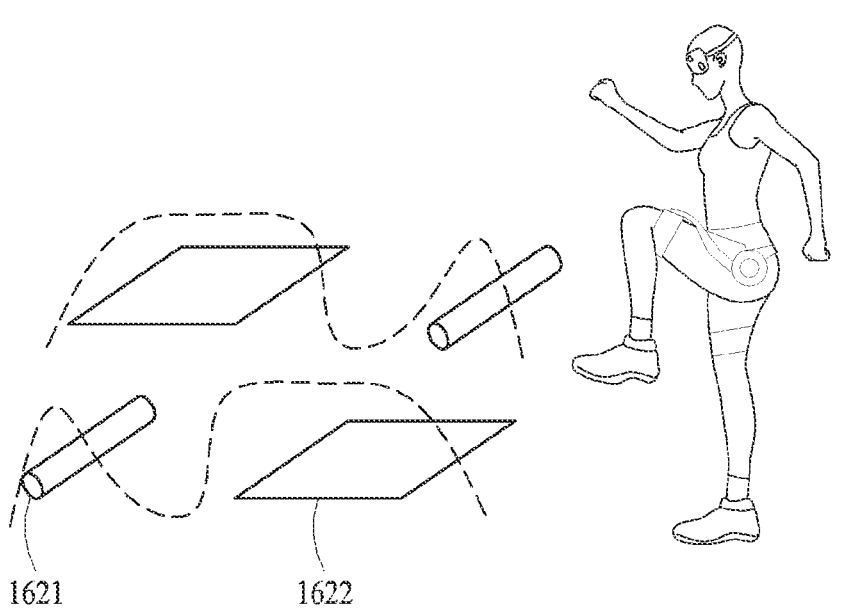
FIGS. 16B, 16C, and 16D are diagrams illustrating example transformations of a virtual object according to an example embodiment.
Figure 16C:
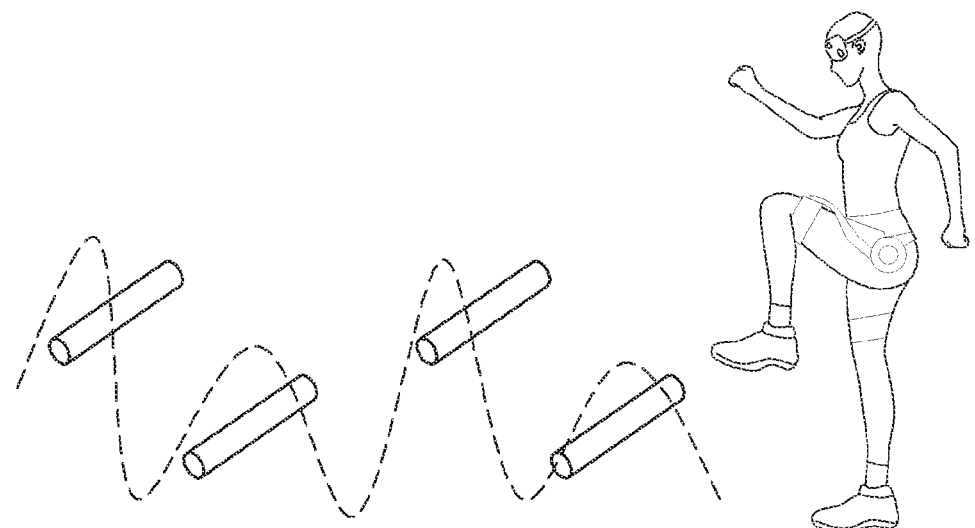
Figure 16D:
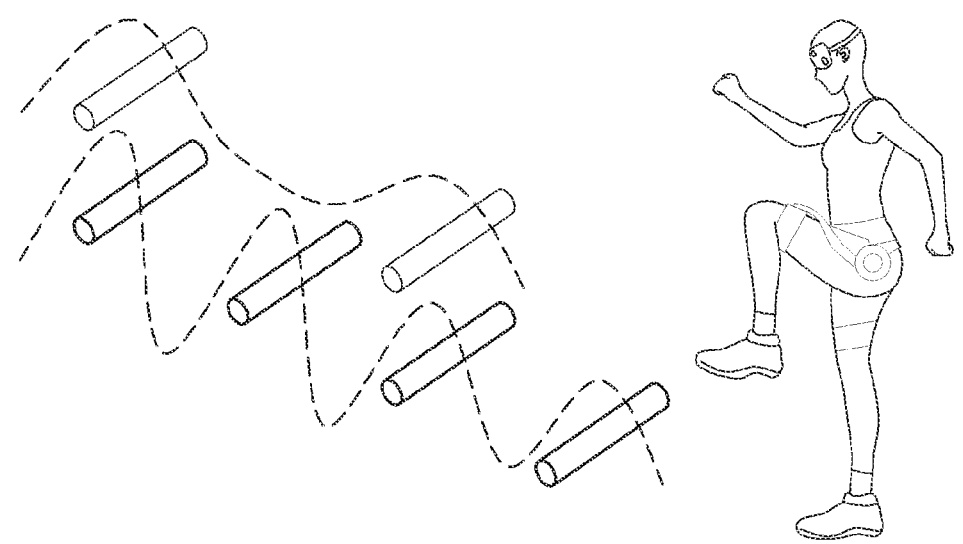

FIGS. 16B, 16C, and 16D are diagrams illustrating example transformations of a virtual object according to an example embodiment. FIG. 16B illustrates an example of adjusting a size of a virtual object. Referring to FIG. 16B, a virtual object 1622 is larger than a virtual object 1621 in size. In this case, an exercise intensity according to the virtual object 1622 may be higher than an exercise intensity according to the virtual object 1621. A long width of the virtual object 1622 may improve a user's ability to maintain a posture. FIG. 16C illustrates an example of adjusting a height of a virtual object. Referring to FIG. 16C, virtual objects having different heights may be provided. Through the example of FIG. 16C, a user's motion range of an exercise may be gradually improved.

FIG. 16D illustrates an example of providing virtual objects of different patterns to both body parts (e.g., a left leg and a right leg). In the example of FIG. 16D, a left intensity range for a left body part of a user and a right intensity range for a right body part of the user may be separately stored as a personal exercise intensity range. In this case, providing an exercise program and measuring a posture score may be independently performed for the left intensity range and the right intensity range. In the example of FIG. 16D, both body parts may have different exercise effects. For example, when one body part is weaker than the other body part, performing an exercise program according to the weak body part may obtain balance in exercise capacity between both body parts.

Figure 17A:
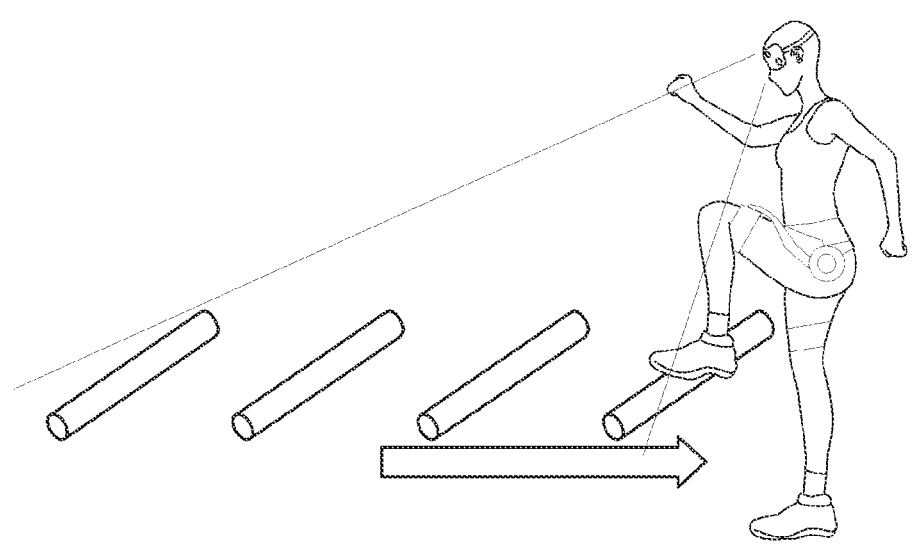
FIGS. 17A and 17B are diagrams illustrating example exercise methods using a virtual object according to an example embodiment.
Figure 17B:
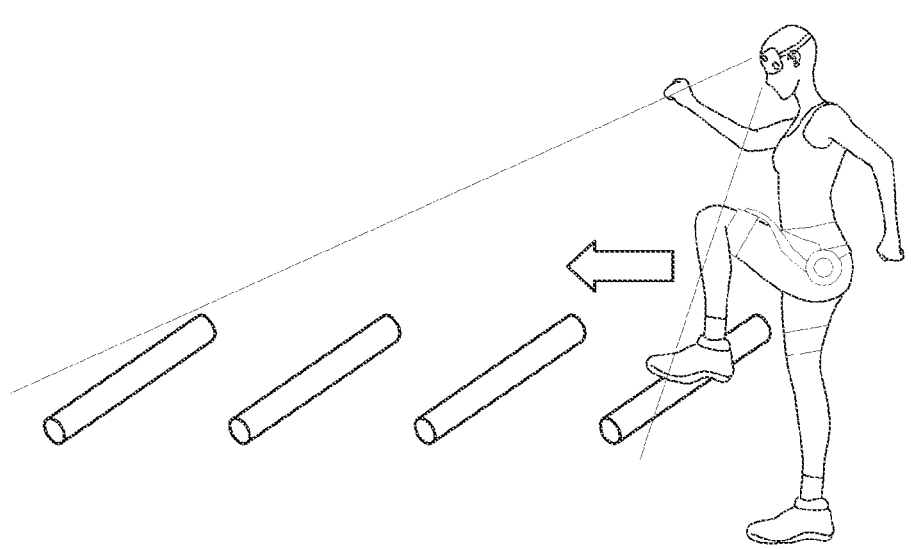

FIGS. 17A and 17B are diagrams illustrating example exercise methods using a virtual object according to an example embodiment. FIG. 17A illustrates virtual objects approaching a user. The user may step over the virtual objects in the same position. FIG. 17B illustrates virtual objects being fixed. The user may step over the virtual objects while approaching them. The example of FIG. 17A may be suitable for an indoor exercise. The example of FIG. 17B may be suitable for an outdoor exercise.

Figure 18:
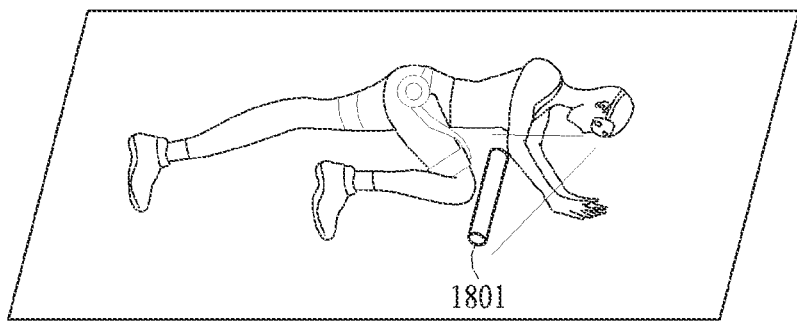
FIG. 18 is a diagram illustrating an example exercise program to be performed on the ground according to an example embodiment.

FIG. 18 is a diagram illustrating an example exercise program to be performed on the ground according to an example embodiment. Referring to FIG. 18, a user may alternately extend both knees toward a virtual object 1801 while lying face down on the ground. According to an exercise method shown in FIG. 18, unlike an exercise method of stepping over the virtual object 1801, touching the virtual object 1801 with the user's knee may be a correct exercise method.

Figure 19:
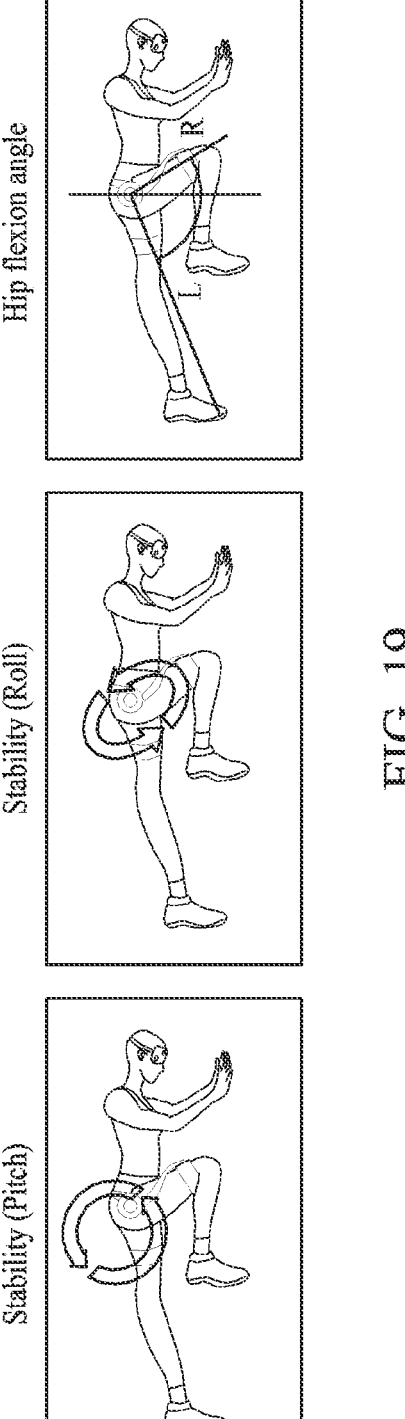
FIG. 19 is a diagram illustrating another example of factors used to adjust an exercise intensity according to an example embodiment.

FIG. 19 is a diagram illustrating another example of factors used to adjust an exercise intensity according to an example embodiment. Referring to FIG. 19, a posture score may be measured according to a posture factor associated with to posture stability of a user. The posture factor associated with the posture stability may include at least some of a pitch-related posture factor, a roll-related posture factor, and a hip flexion angle-related posture factor.

The pitch-related posture factor may indicate whether the pelvis is not excessively tilted forward/backward during a motion. For example, the posture factor of 77° (kyphosis) to 83° (lordosis) may be evaluated as an upper range. The posture factor of 75° to 77° (kyphosis) and 83° to 85° (lordosis) may be evaluated as a middle range. The posture factor in other ranges may be evaluated as a lower range.

The roll-related posture factor may indicate whether the pelvis does not rotate during a motion. For example, the posture factor of 0° to 10° may be evaluated as an upper range. The posture factor of 10° to 20° may be evaluated as a middle range. The posture factor in other ranges may be evaluated as a lower range.

The hip flexion angle-related posture factor may indicate whether a leg is bent and straightened at an appropriate angle. For example, the posture factor of 40° or more (right (R)) and 60° or more (left (L)) may be evaluated as an upper range. The posture factor of 30° to 40° (R) and 50° to 60° (L) may be evaluated as a middle range. The posture factor in other ranges may be evaluated as a middle range.

Each embodiment herein may be used in combination with any other embodiment(s) described herein.

Figure 20:
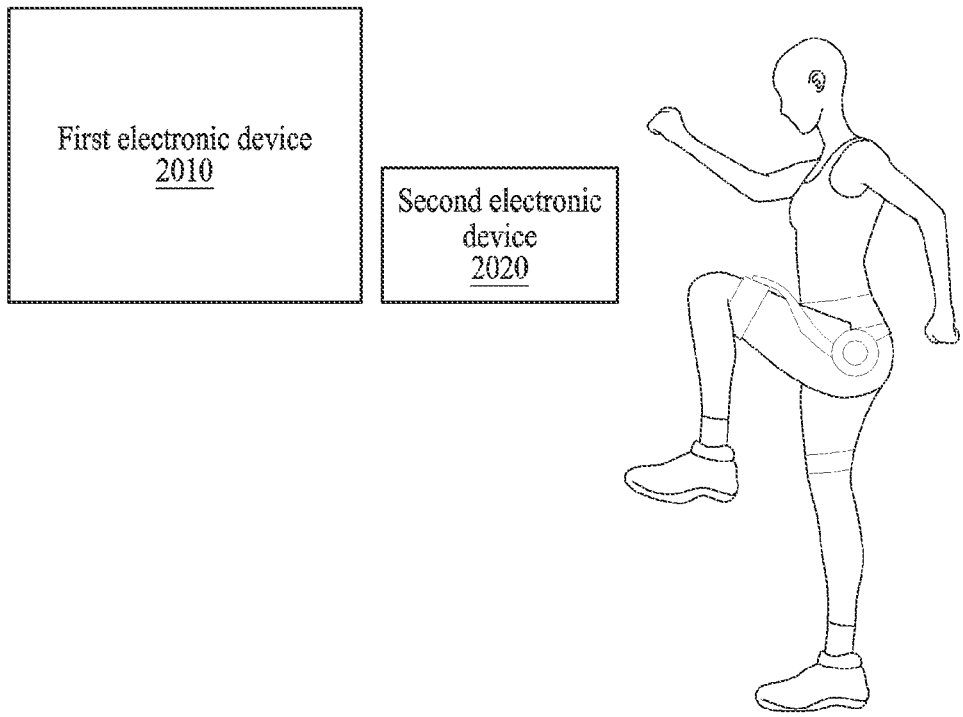
FIG. 20 is a diagram illustrating an example of providing an exercise program without smart glasses according to an example embodiment.

FIG. 20 is a diagram illustrating an example of providing an exercise program without smart glasses according to an example embodiment. Referring to FIG. 20, a first electronic device 2010 may display a virtual object that induces a user to perform a motion. The first electronic device 2010 may be, for example, a non-wearable display device such as a television (TV). A second electronic device 2020 may include a motion recognition sensor (e.g., a camera, a TOF sensor, or an ultrasonic sensor) and may measure the motion of the user using the motion recognition sensor. The first electronic device 2010 may display a current appearance of the user along with the virtual object. The user may perform an exercise program while viewing the first electronic device 2010. In a case in which the first electronic device 2010 has the motion recognition sensor, the exercise program may be provided without the second electronic device 2020. The first electronic device 2010 may further display at least some of a simulation of exercise intensity, a current exercise intensity, a current posture score, a current posture indicator, and an exercise guide.

Figure 21:
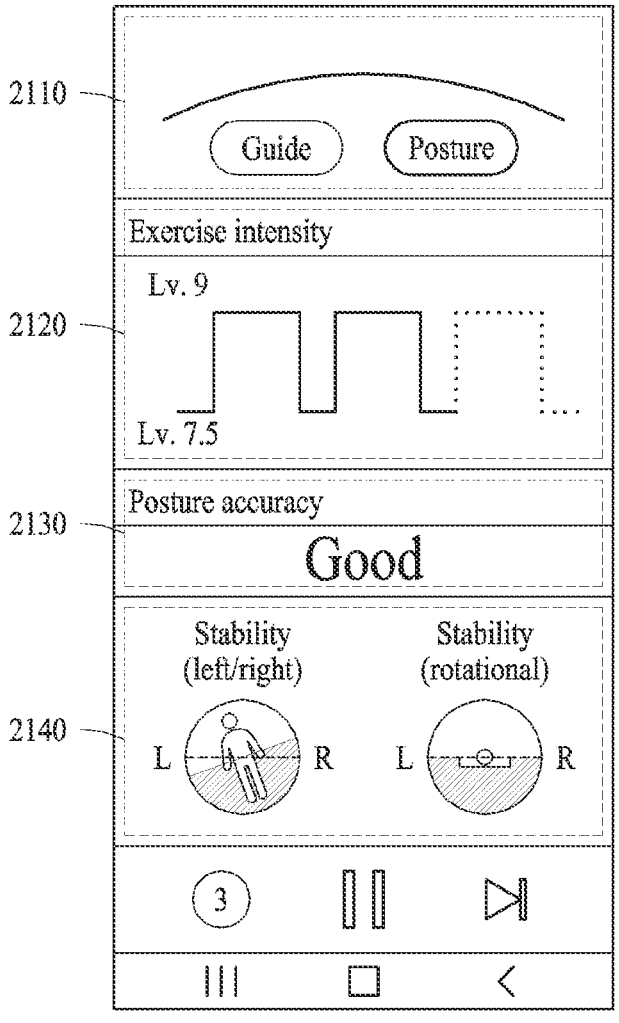
FIG. 21 is a diagram illustrating an example interface screen of an electronic device displaying information about a progress state of an exercise program according to an example embodiment.

FIG. 21 is a diagram illustrating an example interface screen of an electronic device displaying information about a progress state of an exercise program according to an example embodiment. Referring to FIG. 21, an interface screen may include at least some of areas 2110, 2120, 2130, and 2140. The first area 2110 may display an artificial intelligence (AI) image and/or video effect associated with a progress of an exercise program. The second area 2120 may display a simulated exercise intensity and/or a current exercise intensity. The third area 2130 may display a current posture score. The fourth area 2140 may display a current posture indicator.

Figure 22:
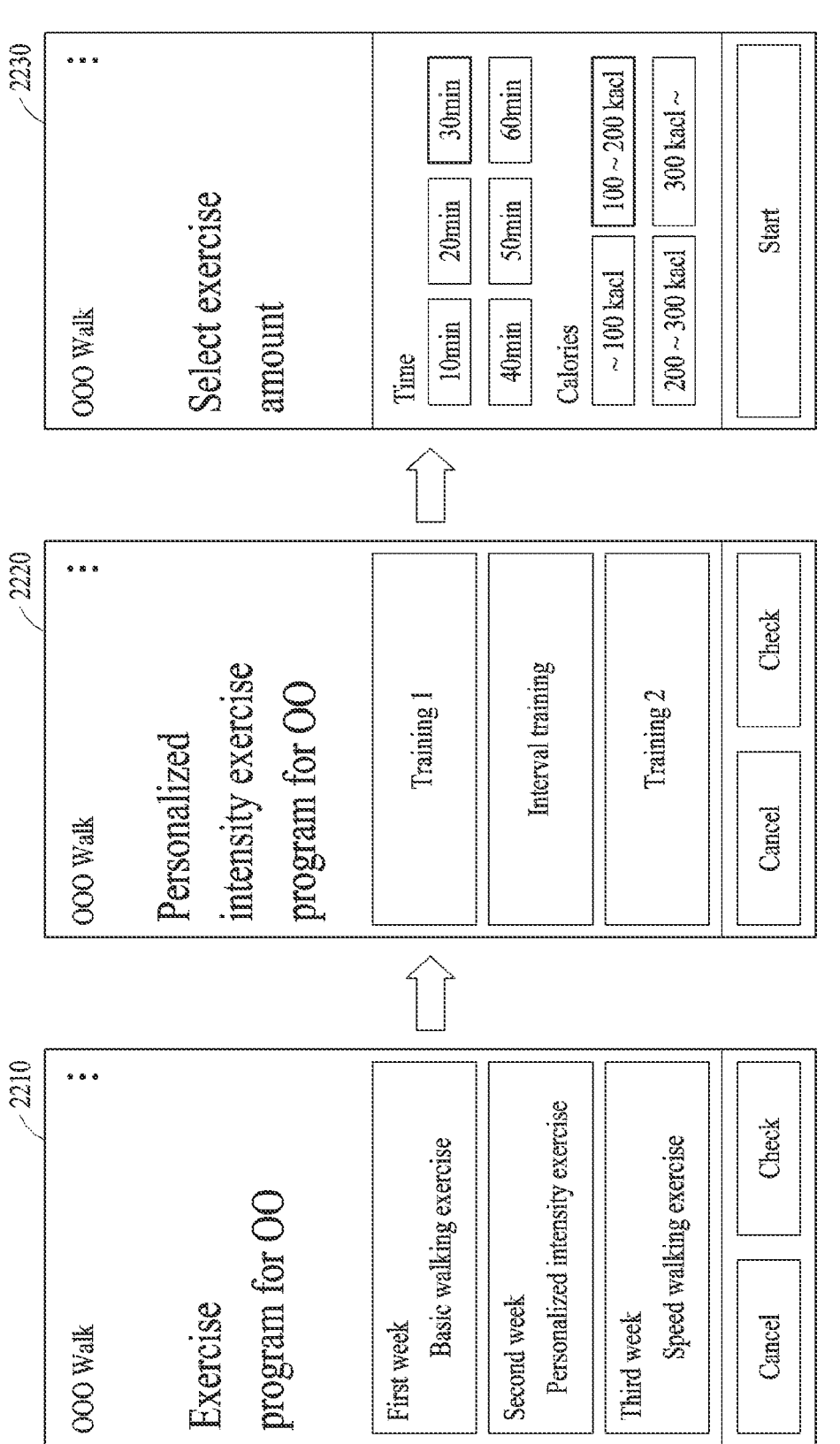
FIG. 22 is a diagram illustrating an example interface screen of an electronic device displaying a menu for selecting an exercise program according to an example embodiment.

FIG. 22 is a diagram illustrating an example interface screen of an electronic device displaying a menu for selecting an exercise program according to an example embodiment. Referring to FIG. 22, a first screen 2210 may display information about a progress of an exercise program. A second screen 2220 may display an exercise program that a user is able to perform in a current round. A third screen 2230 may display a menu for selecting an amount of exercise.

According to various example embodiments, it is possible for a user to easily measure a physical ability by themselves using the wearable device 100 and the electronic device 210 without a separate measurer and expensive measuring equipment. According to the example embodiments, the user may receive a relatively accurate result of an evaluation of their walking ability, muscular strength, fall possibility, balance power, and the like.

It should be appreciated that various example embodiments of the present disclosure and the terms used therein are not intended to limit the technological features set forth herein to particular embodiments but include various changes, equivalents, or replacements for a corresponding embodiment. In connection with the description of the drawings, like reference numerals may be used for similar or related components. It is to be understood that a singular form of a noun corresponding to an item may include one or more of the things unless the relevant context clearly indicates otherwise. As used herein, "A or B," "at least one of A and B," "at least one of A or B," "A, B, or C," "at least one of A, B, and C," and "A, B, or C," each of which may include any one of the items listed together in the corresponding one of the phrases, or all possible combinations thereof. Terms such as "first," "second," or "initial" or "next" or "subsequent" may simply be used to distinguish the component from other components in question, and do not limit the components in other aspects (e.g., importance or order). It is to be understood that if an element (e.g., a first element) is referred to, with or without the term "operatively" or "communicatively," as "coupled with," "coupled to," "connected with," or "connected to" another element (e.g., a second element), the element may be coupled with the other element directly (e.g., by wire), wirelessly, or via at least a third element(s).

As used in connection with various example embodiments of the disclosure, the term "module" may include a unit implemented in hardware, software, or firmware, or any combination thereof, and may interchangeably be used with other terms, for example, "logic," "logic block," "part," or "circuitry." A module may be a single integral component, or a minimum unit or part thereof, adapted to perform one or more functions. For example, according to an example embodiment, the module may be implemented in the form of an application-specific integrated circuit (ASIC). Thus, each "module" herein may comprise circuitry.

Software may include a computer program, a piece of code, an instruction, or some combination thereof, to independently or collectively instruct or configure the processing device to operate as desired. The software and/or data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums. Various example embodiments set forth herein may be implemented as software including one or more instructions that are stored in a storage medium (e.g., the memory 514) that is readable by a machine. For example, a processor of the machine may invoke at least one of the one or more instructions stored in the storage medium and execute it. This allows the machine to be operated to perform at least one function according to the at least one instruction invoked. The one or more instructions may include code generated by a compiler or code executable by an interpreter. The machine-readable storage medium may be provided in the form of a non-transitory storage medium. Here, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to various example embodiments, a method according to an example embodiment of the disclosure may be included and provided in a computer program product. The computer program product may be traded as a product between a seller and a buyer. The computer program product may be distributed in the form of a machine-readable storage medium (e.g., a compact disc read-only memory (CD-ROM)), or be distributed (e.g., downloaded or uploaded) online via an application store (e.g., PlayStore™) or between two user devices (e.g., smart phones) directly. If distributed online, at least part of the computer program product may be temporarily generated or at least temporarily stored in the machine-readable storage medium, such as a memory of the manufacturer's server, a server of the application store, or a relay server.

According to various example embodiments, each component (e.g., a module or a program) of the above-described components may include a single entity or multiple entities, and some of the multiple entities may be separately disposed in different components. According to various example embodiments, one or more of the above-described components or operations may be omitted, or one or more other components or operations may be added. Alternatively or additionally, a plurality of components (e.g., modules or programs) may be integrated into a single component. In such a case, according to various example embodiments, the integrated component may still perform one or more functions of each of the plurality of components in the same or similar manner as they are performed by a corresponding one of the plurality of components before the integration. According to various example embodiments, operations performed by the module, the program, or another component may be carried out sequentially, in parallel, repeatedly, or heuristically, or one or more of the operations may be executed in a different order or omitted, or one or more other operations may be added.

While the disclosure has been illustrated and described with reference to various embodiments, it will be understood that the various embodiments are intended to be illustrative, not limiting. It will further be understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:

1. An electronic device, comprising:
a wearable device comprising a frame configured to be worn on a body of a user and a driving module configured to generate an exercise load applied to said frame for a motion of the user;
a communication module, comprising communication circuitry, configured to communicate with the wearable device; and
a processor, comprising processing circuitry, configured to:
provide a first exercise program of a first exercise period by changing an exercise intensity within an initial exercise intensity range for a user of the wearable device based on controlling the exercise load of the user through the wearable device, the first exercise period corresponding to a warm-up exercise period;
measure a first posture score of the user while the user is performing the first exercise program, the first posture score being determined based on one or more posture factors specific to a posture required by the first exercise program;
determine an exercise ability of the user for the first exercise program by comparing the first posture score to a posture boundary value set for the first exercise program;
set a personal exercise intensity range of the user based on a result of the compare; and
provide a second exercise program of a second exercise period based on the personal exercise intensity range, the second exercise period corresponding to a personalized exercise program period different from the warm-up exercise period of the first exercise period.

2. The electronic device of claim 1, wherein the posture boundary value comprises an upper boundary value and a lower boundary value, and
the personal exercise intensity range is based on an upper intensity value and a lower intensity value.

3. The electronic device of claim 2, wherein, to set the personal exercise intensity, the processor is configured to:
in response to the first posture score and the upper boundary value crossing at a first time point, by a change in a current exercise intensity of the first exercise program, set a first current exercise intensity at the first time point as the lower intensity value; and
in response to the first posture score and the lower boundary value crossing at a second time point, by a change in the current exercise intensity of the first exercise program, set a second current exercise intensity at the second time point as the upper intensity value.

4. The electronic device of claim 1, wherein, to provide at least one of the first exercise program or the second exercise program, the processor is configured to:
control to display a virtual object on a display device to induce the user to perform a motion; and
generate an exercise load for the motion of the user through the wearable device.

5. The electronic device of claim 4, wherein at least a portion of the initial exercise intensity range and the personal exercise intensity range is based on a first intensity factor associated with the virtual object and a second intensity factor associated with the exercise load.

6. The electronic device of claim 5, wherein the first intensity factor is based on at least one of:
a first sub-intensity factor associated with a distance between a center of weight of the user and the virtual object;
a second sub-intensity factor associated with a distance between neighboring virtual objects comprising the virtual object;
a third sub-intensity factor associated with a height of the virtual object;
a fourth sub-intensity factor associated with a size of the virtual object; and
a fifth sub-intensity factor associated with a moving speed of the virtual object.

7. The electronic device of claim 5, wherein the first intensity factor is based on a parameter that is based on at least one of: a depth of water, a direction of water current, or a speed of water current in an underwater environment in an aqua mode.

8. The electronic device of claim 4, wherein at least one of the first posture score or a second posture score is based on a first posture factor associated with posture stability of the user and a second posture factor associated with a distance between the user and the virtual object.

9. The electronic device of claim 1, wherein, to provide the second exercise program, the processor is configured to:
measure a second posture score of the user while the user is performing the second exercise program; and
in response to the second posture score being out of a control margin of the posture boundary value, adjust a current exercise intensity of the second exercise program.

10. The electronic device of claim 9, wherein the posture boundary value comprises an upper boundary value and a lower boundary value,
for the upper boundary value, a first upper control margin and a first lower control margin are set, and
the personal exercise intensity range is based on an upper intensity value and a lower intensity value,
wherein, to adjust the current exercise intensity of the second exercise program, the processor is configured to:
in response to the second posture score exceeding the first upper control margin, increase the current exercise intensity of the second exercise program; and in response to the second posture score becoming less than the first lower control margin as the current exercise intensity increases, stop increasing the current exercise intensity.

11. The electronic device of claim 10, wherein the processor is configured so that, for the lower boundary value, a second upper control margin and a second lower control margin are set, wherein, to adjust the current exercise intensity of the second exercise program, the processor is configured to:

in response to the second posture score being less than the second lower control margin, decrease the current exercise intensity of the second exercise program; and in response to the second posture score exceeding the second upper control margin as the current exercise intensity decreases, stop decreasing the current exercise intensity.

12. The electronic device of claim 9, wherein, to adjust the current exercise intensity of the second exercise program, the processor is configured to:

adjust in real time the current exercise intensity of the second exercise program as the second posture score is out of the control margin of the posture boundary value.

13. The electronic device of claim 9, wherein the personal exercise intensity range comprises a left intensity range for a left body part of the user and a right intensity range for a right body part of the user.

14. The electronic device of claim 13, wherein the processor is configured so that providing the second exercise program and measuring the second posture score are performed independently for the left intensity range and the right intensity range.

15. A control method, comprising:

providing a first exercise program of a first exercise period by changing an exercise intensity within an initial exercise intensity range to a user wearing a wearable device comprising a frame configured to be worn on a body of a user and a driving module configured to generate an exercise load applied to said frame for a motion of the user for exercise based on controlling the exercise load of the user through the wearable device, the first exercise period corresponding to a warm-up exercise period;

measuring a first posture score of the user while the user is performing the first exercise program using the wearable device, the posture score being determined based on one or more posture factors specific to a posture required by the first exercise program;

determining an exercise ability of the user for the first exercise program by comparing the first posture score to a posture boundary value set for the first exercise program;

setting a personal exercise intensity range of the user based on a result of the comparing; and providing a second exercise program of a second exercise period based on the personal exercise intensity range, the second exercise period corresponding to a personalized exercise program period different from the warm-up exercise period of the first exercise period, wherein the operation of providing the second exercise program comprises:

measuring a second posture score of the user while the user is performing the second exercise program using the wearable device; and in response to the second posture score being out of a control margin of the posture boundary value, adjusting a current exercise intensity of the second exercise program.

16. The control method of claim 15, wherein the posture boundary value comprises an upper boundary value and a lower boundary value, and the personal exercise intensity range is based on an upper intensity value and a lower intensity value, wherein the setting the personal exercise intensity range comprises:

in response to the first posture score and the upper boundary value crossing at a first time point by a change in a current exercise intensity of the first exercise program, setting a first current exercise intensity at the first time point as the lower intensity value; and in response to the first posture score and the lower boundary value crossing at a second time point, by a change in the current exercise intensity of the first exercise program, setting a second current exercise intensity at the second time point as the upper intensity value.

17. The control method of claim 15, wherein at least a portion of the providing the first exercise program and the operation of providing the second exercise program comprises:

displaying a virtual object on a display to induce the user to perform a motion; and generating an exercise load for the motion of the user via the wearable device.

18. The control method of claim 15, wherein the posture boundary value comprises an upper boundary value and a lower boundary value, for the upper boundary value, a first upper control margin and a first lower control margin are set, and the personal exercise intensity range is determined by an upper intensity value and a lower intensity value, wherein the adjusting the current exercise intensity of the second exercise program comprises:

in response to the second posture score becoming less than the first lower control margin as the current exercise intensity increases, stopping increasing the current exercise intensity.

19. A wearable device to be worn by a user, the wearable device comprising:

a leg support frame configured to support a leg of the user;

a driving module, comprising at least one of a motor and circuitry, configured to generate an exercise load applied to said leg support frame for a motion of the user; and at least one processor configured to:

provide a first exercise program of a first exercise period by changing an exercise intensity within an initial exercise intensity range based on controlling the exercise load of the user through the driving module and leg support frame, the first exercise period corresponding to a warm-up exercise period;

measure a first posture score of the user while the user is performing the first exercise program via the wearable device, the first posture score being determined based on one or more posture factors including at least one of a pitch-related posture factor indicating forward/backward tilt of the user's pelvis, a roll-related posture factor indicating whether the pelvis is parallel to the ground, a yaw-related posture factor indicating pelvic rotation during motion, a posture factor based on a distance between the user and virtual content, and a posture factor based on angular velocity;

compare the first posture score to a posture boundary value;

set a personal exercise intensity range of the user based on a result of the comparing; and provide a second exercise program of a second exercise period based on the personal exercise intensity range, the second exercise period corresponding to a personalized exercise program period different from the warm-up exercise period of the first exercise period.

20. The wearable device of claim 19, wherein the posture boundary value comprises an upper boundary value and a lower boundary value, and the personal exercise intensity range is based on an upper intensity value and a lower intensity value.

\* \* \* \* \*